US011694786B1

(12) United States Patent
Van Wilt et al.

(10) Patent No.: US 11,694,786 B1
(45) Date of Patent: Jul. 4, 2023

(54) RECOMMENDATION METHODS, SYSTEMS AND DEVICES

(71) Applicants: Yasmine Van Wilt, New York, NY (US); Kenneth Bahk, Glenview, IL (US)

(72) Inventors: Yasmine Van Wilt, New York, NY (US); Kenneth Bahk, Glenview, IL (US)

(*) Notice: Subject to any disclaimer, the term of this patent is extended or adjusted under 35 U.S.C. 154(b) by 13 days.

(21) Appl. No.: 16/735,610

(22) Filed: Jan. 6, 2020

Related U.S. Application Data

(60) Provisional application No. 62/788,908, filed on Jan. 6, 2019, provisional application No. 62/788,656, filed on Jan. 4, 2019.

(51) Int. Cl.
*G16H 20/70* (2018.01)
*G06Q 30/0601* (2023.01)
(Continued)

(52) U.S. Cl.
CPC ............ *G16H 20/70* (2018.01); *A61M 21/02* (2013.01); *G06F 16/435* (2019.01); *G06N 3/004* (2013.01);
(Continued)

(58) Field of Classification Search
CPC ........ G16H 20/70; G16H 10/60; G16H 15/00; G16H 10/20; G16H 20/60; G16H 70/20;
(Continued)

(56) References Cited

U.S. PATENT DOCUMENTS 6,689,816 B2 *  2/2004  Fogel ................... A61P 25/22
                                                      514/704
9,736,603 B2    8/2017  Osborne et al.
(Continued)

FOREIGN PATENT DOCUMENTS

WO    WO 2019/097236 A1    5/2019

OTHER PUBLICATIONS

Al-Nabki et al., Improving named entity recognition in noisy user-generated text with local distance neighbor feature, Neurocomputing, 382 (2020) 1-11; https://doi.org/10.1016/j.neucom.2019.11.072.
(Continued)

*Primary Examiner* — Michael Tomaszewski
(74) *Attorney, Agent, or Firm* — Cooley LLP

(57) ABSTRACT

Some embodiments of the present disclosure relate to systems, devices, and methods for making recommendations to users for, individually or together, goods, services, and information/media (e.g., audio, video, publications), as well as verifying the veracity of data/information, based upon an emotional impact of such goods/services and/or media/information on the user, other users, and/or other individuals, as well some embodiments directed to systems, devices, and methods for treating one or more brain functions, including neurological conditions and episodes associated therewith by determining (and optionally providing) media (e.g., audio, but in some embodiments, any of audio, textual information, and video), which may be referred to as optimal medical media ("OMM").

15 Claims, 6 Drawing Sheets

(51) Int. Cl.
  G06Q 20/12 (2012.01)
  G06Q 30/0203 (2023.01)
  G16H 10/60 (2018.01)
  G16H 10/20 (2018.01)
  G16H 70/20 (2018.01)
  G16H 20/60 (2018.01)
  G16H 15/00 (2018.01)
  G06Q 50/26 (2012.01)
  G06F 16/435 (2019.01)
  G06N 3/004 (2023.01)
  G06N 5/04 (2023.01)
  A61M 21/02 (2006.01)
  G06Q 30/0204 (2023.01)
  A61M 21/00 (2006.01)

(52) U.S. Cl.
  CPC ............ *G06N 5/04* (2013.01); *G06Q 20/123* (2013.01); *G06Q 30/0203* (2013.01); *G06Q 30/0204* (2013.01); *G06Q 30/0631* (2013.01); *G06Q 50/265* (2013.01); *G16H 10/20* (2018.01); *G16H 10/60* (2018.01); *G16H 15/00* (2018.01); *G16H 20/60* (2018.01); *G16H 70/20* (2018.01); *A61M 2021/005* (2013.01); *A61M 2021/0027* (2013.01)

(58) Field of Classification Search
  CPC ................ G06F 16/435; A61M 21/02; A61M 2021/0027; A61M 2021/005; G06N 3/004; G06N 5/04; G06Q 20/123; G06Q 30/0203; G06Q 30/0204; G06Q 30/0631; G06Q 50/265
  See application file for complete search history.

(56) References Cited

U.S. PATENT DOCUMENTS

| | | | |
|---|---|---|---|
| 10,587,967 B2 | 3/2020 | Osborne et al. | |
| 2010/0063427 A1* | 3/2010 | Ingrao | A61H 1/003 601/90 |
| 2011/0245586 A1* | 10/2011 | Slane | A61M 21/02 600/28 |
| 2013/0297536 A1* | 11/2013 | Almosni | G16H 50/20 706/12 |
| 2014/0052475 A1* | 2/2014 | Madan | G16H 50/30 705/3 |
| 2014/0307878 A1 | 10/2014 | Osborne et al. | |
| 2016/0007905 A1* | 1/2016 | Milner | G16H 50/20 434/262 |
| 2016/0077547 A1* | 3/2016 | Aimone | A61B 5/1114 345/8 |
| 2017/0235912 A1* | 8/2017 | Moturu | G16H 40/67 705/2 |
| 2019/0043619 A1* | 2/2019 | Vaughan | G16H 50/20 |
| 2019/0260703 A1* | 8/2019 | Moskowitz | G06F 16/90324 |
| 2020/0213790 A1 | 7/2020 | Osborne et al. | |
| 2020/0286505 A1 | 9/2020 | Osborne et al. | |

OTHER PUBLICATIONS

Bagherzadeh et al., Emotion Recognition Using Continuous Wavelet Transform and Ensemble of Convolutional Neural Networks through Transfer Learning from Electroencephalogram Signal, Frontiers in Biomedical Technologies, vol. 10, No. 1 (Winter 2023) 47-56.
Cano et al., Crowdsourcing Emotions in Music Domain, International Journal of Artificial Intelligence and Applications (IJAIA), vol. 8, No. 4, Jul. 2017.
Emami et al., Vitamin D suppresses proangiogenic factors in patients with ulcerative colitis: A randomized double blind placebo controlled clinical trial, Complementary Therapies in Clinical Practice, 39 (2020), 101086; https://doi.org/10.1016/j.ctcp.2020.101086.
Eerola, Are the Emotions Expressed in Music Genre-specific? An Audio-based Evaluation of Datasets Spanning Classical, Film, Pop and Mixed Genres, Journal of New Music Research 2011, vol. 40, No. 4, pp. 349-366.
Gligic et al., Named entity recognition in electronic health records using transfer learning bootstrapped Neural Networks, Neural Networks 121 (2020) 132-139; https://doi.org/10.1016/j.neunet.2019.08.032.
Greco et al., Emotions and Mood States: Modeling, Elicitation, and Recognition, Emotions and Mood States: Modeling, Elicitation, and Recognition, 2019; https://link.springer.com/chapter/10.1007%2F978-3-319-46705-4_4, 17 pages.
Gutierrez-Cobo et al., The Three Models of Emotional Intelligence and Performance in a Hot and Cool go/no-go Task in Undergraduate Students, Front. Behav. Neurosci., Feb. 22, 2017 Sec. Emotion Regulation and Processing, vol. 11—2017; https://doi.org/10.3389/fnbeh.2017.00033, 13 pages.
Han et al., Power scheduling optimization under single-valued neutrosophic uncertainty, Neurocomputing, 382 (2020) 12-20; https://doi.org/10.1016/j.neucom.2019.11.089.
Haq et al., Speaker-Dependent Audio-Visual Emotion Recognition, AVSP 2009—International Conference on Audio-Visual Speech Processing University of East Anglia, Norwich, UK, Sep. 10-13, 2009; http://www.isca-speech.org/archive, 6 pages.
Hazarika et al., ICON: Interactive Conversational Memory Network for Multimodal Emotion Detection, Proceedings of the 2018 Conference on Empirical Methods in Natural Language Processing, pp. 2594-2604, Brussels, Belgium, Oct. 31-Nov. 4, 2018.
Hu et al., Essential Role of MeCP2 in the Regulation of Myofibroblast Differentiation during Pulmonary Fibrosis, The American Journal of Pathology, vol. 178, No. 4, Apr. 2011.
Kinugawa et al., Aging-related episodic memory decline: are emotions the key?, Front. Behav. Neurosci., vol. 7, Article 2, 2013; https://doi.org/10.3389/fnbeh.2013.00002, 12 pages.
Kosta et al., A Study of Cultural Dependence of Perceived Mood in Greek Music, InISMIR Nov. 2013, 317-322, 6 pages.
Luo, Forecasting fund-related textual emotion trends on Weibo: A time series study, Front. Commun., Dec. 16, 2022, Sec. Advertising and Marketing Communication Volume 7—2022; https://doi.org/10.3389/fcomm.2022.970749, 13 pages.
Miyamoto et al., Applying Meta-Learning and Iso Principle for Development of EEG-Based Emotion Induction System, Front. Digit. Health 4:873822; doi: 10.3389/fdgth.2022.873822, 14 pages.
MacDorman et al., Automatic Emotion Prediction of Song Excerpts: Index Construction, Algorithm Design, and Empirical Comparison, Journal of New Music Research 2007, vol. 36, No. 4, pp. 283-301.
Nardone et al., Music therapy and radiation oncology: State of art and future directions, Complementary Therapies in Clinical Practice, 39 (2020) 101124; https://doi.org/10.1016/j.ctcp.2020.101124, 7 pages.
Ng et al., No improvement in disclosure of natural health product use to primary care medical doctors in the last 15 years: A survey of naturopathic patients, Complementary Therapies in Clinical Practice, 39 (2020) 101106; https://doi.org/10.1016/j.ctcp.2020.101106, 7 pages.
Pan et al., Multi-modal Attention for Speech Emotion Recognition, Accepted by Interspeech2020 doi.org/10.48550/arxiv.2009.04107, 5 pages.
Park et al., K-EmoCon, A Multimodal Sensor Dataset for Continuous Emotion Recognition in Naturalistic Conversations, Sci Data 7, (2020) 293; arXiv:2005.04120v2 [cs.HC] May 19, 2020, 20 pages.
Perez et al., The emerging healthcare professional: Certified yoga therapist (C-IAYT), Complementary Therapies in Clinical Practice, 39 (2020) 101147; https://doi.org/10.1016/j.ctcp.2020.101147, 8 pages.
Ros et al., Consensus on the reporting and experimental design of clinical and cognitive-behavioural neurofeedback studies (CRED-nf checklist), Brain 2020:143; 1674-1685.
Sacco, Fibonacci Harmonics: A New Mathematical Model of Synchronicity, Applied Mathematics, 2018, 9, 702-718.

(56) References Cited

OTHER PUBLICATIONS

Szpunar et al., Memories of the future: new insights into the adaptive value of episodic memory, Front. Behav. Neurosci., May 23, 2013 Sec. Learning and Memory vol. 7—2013; https://doi.org/10.3389/fnbeh.2013.00047, 3 pages.
Thomas et al., Brain imaging correlates of cognitive impairment in depression, Frontiers in Human Neuroscience, vol. 3, Article 30 (2009); doi: 10.3389/neuro.09.030.2009, 9 pages.
Uyanik et al., Use of Differential Entropy for Automated Emotion Recognition in a Virtual Reality Environment with EEG Signals, Diagnostics 2022, 12, 2508; https://doi.org/10.3390/diagnostics12102508, 14 pages.
Xiaofeng et al., Incorporating token-level dictionary feature into neural model for named entity recognition, Neurocomputing, 375 (2020) 43-50; https://doi.org/10.1016/j.neucom.2019.09.005.
Xiu et al., Emotional face expression modulates occipital-frontal effective connectivity during memory formation in a bottom-up fashion, Front. Behav. Neurosci., Apr. 23, 2015, Sec. Learning and Memory, vol. 9—2015; https://doi.org/10.3389/fnbeh.2015.00090, 11 pages.
Zacarias-Morales et al., Attention-Inspired Artificial Neural Networks for Speech Processing: A Systematic Review, Symmetry 2021, 13, 214; https://doi.org/10.3390/sym13020214, 43 pages.
Ahmadi et al., A dual approach for positive T-S fuzzy controller design and its application to cancer treatment under immunotherapy and chemotherapy Biomedical Signal Processing and Control, 9 pages. vol. 58, Apr. 2020, 101822.
Ahn et al., Orbitofrontal cortex functional connectivity changes in patients with binge eating disorder and bulimia nervosa, 12 pages. PLoS One. Dec. 28, 2022;17(12):e0279577. doi: 10.1371/journal.pone.0279577.
Aitchison et al., Six adolescents' lived experiences of resource-oriented music therapy assessment in a community-based mental health day program, The Arts in Psychotherapy; 10 pages. vol. 82, Feb. 2023, 101991.
Alink et al., "Forward models demonstrate that repetition suppression is best modelled by local neural scaling" NatCommun 9, 3854, 10 pages. (2018).
Altantawy et al., Bi-perspective Fisher discrimination for single depth map upsampling: A self-learning classification-based approach, Neurocomputing, vol. 380, 2020, pp. 321-340.
Alves et al., The subcortical and neurochemical organization of the ventral and dorsal attention networks, Commun Biol. Dec. 7, 2022; 5(1): 1343, 14 pages.
Andrade et al., Integration of thermodynamic, quantum and hierarchical theories of information in the context of Peircean semiosis—a review Biosystems, 11 pages. Jun. 2014; 120:10-20. doi: 10.1016/j.biosystems.2014.04.001. Epub Apr. 13, 2014.
Ankishan et al., Blood Pressure prediction from speech recordings, Biomedical Signal Processing and Control, 9 pages. Volume 58, Apr. 2020, 101842.
Arteaga et al., EMG-driven hand model based on the classification of individual finger movements, Biomedical Signal Processing and Control, 10 pages. vol. 58, Apr. 2020, 101834.
Babu et al., Optimized feature selection for the classification of uterine magnetomyography signals for the detection of term delivery, Biomedical Signal Processing and Control, 7 pages. vol. 58, Apr. 2020, 101880.
Bari et al., Epileptic seizure detection in EEG signals using normalized IMFs in CEEMDAN domain and quadratic discriminant classifier, Biomedical Signal Processing and Control, 8 pages. vol. 58, Apr. 2020, 101833.
Bertolaccini et al., Thoracic surgeons, mathematics, and statisticians: a new multidisciplinary team?, J Vis Surg. Jan. 2017; 3: 5, 5 pages.
Biro et al.,The neural correlates of context driven changes in the emotional response: An fMRI study, PLoS One. 20 pages. Dec. 30, 2022; 17(12): e0279823. doi: 10.1371/journal.pone.0279823.

Bong et al., Implementation of wavelet packet transform and non linear analysis for emotion classification in stroke patient using brain signals, Biomedical Signal Processing and Control vol. 36, Jul. 2017, pp. 102-112.
Bornemann et al., Voluntary upregulation of heart rate variability through biofeedback is improved by mental contemplative training, Sci Rep 9, 7860, 2019, 13 pages.
Cai, Sequoia Doubles Down On Seed Investing To Hunt For The Unicorns Unique To Downturns, Forbes, Jan. 2023, 6 pages, https://www.forbes.com/sites/kenrickcai/2023/01/18/sequoia-new-seed-fund-and-arc-expansion/?sh=1afeca4c696e.
Caetano, M. et al., "Theoretical framework of a computational model of auditory memory for music emotion recognition." Proceedings of the 15th Conference of the International Society for Music Information Retrieval, 2014, 6 pages.
Caruso et al., Single neurons may encode simultaneous stimuli by switching between activity patterns, 16 pages. NatCommun. Jul. 13, 2018; 9(1): 2715. doi: 10.1038/s41467-018-05121-8.
Chandra et al., Fractional mesh-free linear diffusion method for image enhancementand segmentation for automatic tumor classification, Biomedical Signal Processing and Control, 9 pages. vol. 58, Apr. 2020, 101841.
Chen et al., EEG-based emotion recognition using simple recurrent units networkand ensemble learning, Biomedical Signal Processing and Control, 13 pages. vol. 58, Apr. 2020, 101756.
Chen et al., Quantum-dot cellular automata as a potential technology for designing nano-scale computers: Exploring the state-of-the-art techniques and suggesting the opportunities for the future, Optik, 13 pages. vol. 265, Sep. 2022, 169431.
Chen et al., "Shared memories reveal shared structure in neural activity across individuals" at Neurosci. Jan. 2017; 20(1): 115-125. doi: 10.1038/nn.4450. Epub Dec. 5, 2016.
Chen et al., Resting-state brain information flow predicts cognitive flexibility in humans, Sci Rep 9, 3879, 2019, 16 pages.
Coecke et al., Graphical Calculus for Quantum Key Distribution (Extended Abstract), Electronic Notes in Theoretical Computer Science; vol. 270, Issue 2, Feb. 14, 2011, pp. 231-249.
Cohn, D., e al., Active learning with statistical models, Journal of artificial intelligence research 4, 1996: pp. 129-145.
De Almeida et al., Spectral F Test for detecting TMS/EEG responses, Biomedical Signal Processing and Control, 11 pages. vol. 58, Apr. 2020, 101840.
Defu, C et al., Toward Recognizing Two Emotion States from ECG Signals, 2009 International Conference on Computational Intelligence and Natural Computing, Wuhan, China, 2009, pp. 210-213.
Deka et al., "Calibrationless joint compressed sensing reconstruction for rapid parallel MRI" Biomedical Signal Processing and Control, 10 pages. vol. 58, Apr. 2020, 101871.
Dere et al., Progress in Episodic Memory Research, Front. Behav. Neurosci., Mar. 30, 2016 Sec. Learning and Memory, vol. 10, 2016; https://doi.org/10.3389/fnbeh.2016.00061, 515 pages.
Derwin et al., A novel automated system of discriminating Microaneurysms in fundus images, Biomedical Signal Processing and Control, 9 pages. vol. 58, Apr. 2020, 101839.
Gouveia et al., Study on the usage feasibility of continuous-wave radar for emotion recognitionm, Biomedical Signal Processing and Control, 10 pages. vol. 58, Apr. 2020, 101835.
Drossos et al., Sound events and emotions: Investigating the relation of rhythmic characteristics and arousal, IISA 2013, Piraeus, Greece, 2013, pp. 1-6.
Feneberg et al., The effects of music listening on somatic symptoms and stress markers in the everyday life of women with somatic complaints and depression, Sci Rep 11, 24062, Dec. 2021, 12 pages.
Feng et al., Semantic parsing of the life process by quantum biology, Progress in Biophysics and Molecular Biology, vol. 175, 2022, pp. 79-89.
Fernandez-Castrom et al., The influence of preoperative anxiety on postoperative pain in patients undergoing cardiac surgery, Sci Rep. Oct. 1, 2022; 12(1):16464, 8 pages.
Fleckenstein et al., A prospective randomized controlled trial assessing the effect of music on patients' anxiety in venous catheter placement procedures, Sci Rep. Apr. 28, 2022; 12(1): 6922, 8 pages.

(56) References Cited

OTHER PUBLICATIONS

Foleis et al., Texture selection for automatic music genre classification, Applied Soft Computing, vol. 89, 2020, 106127, 18 pages.
Garcia et al., Understanding diaschisis models of attention dysfunction with rTMS, Sci Rep. Sep. 10, 2020; 10(1): 14890, 15 pages.
Giordano et al., Effect of single session receptive music therapy on anxiety and vital parameters in hospitalized Covid-19 patients: a randomized controlled trial, Sci Rep. Feb. 24, 2022;12(1):3154, 9 pages.
Gray et al., Information content best characterises the hemispheric selectivity of the inferior parietal lobe: a meta-analysis, Sci Rep. Sep. 15, 2020; 10(1): 15112, 9 pages.
Hagins et al., Motion of the multi-segmented spine in elite dancers during passé and arabesque, Gait Posture. Jul. 2021; 88:198-202. doi: 10.1016/j.gaitpost.2021.05.032. Epub Jun. 6, 2021.
Hajj et al., A review of machine learning techniques in photoplethysmographyfor the non-invasive cuff-less measurement of blood pressure, Biomedical Signal Processing and Control, 14 pages. vol. 58, Apr. 2020, 101870.
Haslbeck et al., Music From the Very Beginning-A Neuroscience-Based Framework for Music as Therapy for Preterm Infants and Their Parents, Front Behav Neurosci, 7 pages. Jun. 5, 2018; 12:112. doi: 10.3389/fnbeh.2018.00112.
He et al., The effect of music therapy on anxiety and pain in patients undergoing prostate biopsy: A systematic review and meta-analysis, Complement Ther Med. 9 pages. Dec. 26, 2022;72:102913. doi: 10.1016/j.ctim.2022.102913.
Herbert et al., Surface roughness characterisation using optical feedback interferometry, Electronics Letters 53.4, 2017, pp. 268-270.
Illner et al., Validation of freely-available pitch detection algorithms across various noise levels in assessing speech captured by smartphone in Parkinson's disease, Biomedical Signal Processing and Control, 13 pages. vol. 58, Apr. 2020, 101831.
Hua et al., Lymph-vascular space invasion prediction in cervical cancer: Exploring radionics and deep learning multilevel features of tumor andperitumor tissue on multiparametric MRI, Biomedical Signal Processing and Control, 7 pages. vol. 58, Apr. 2020, 101869.
Jain et al., Modeling of emotion elicitation conditions for a cognitive-emotive architecture, Cognitive Systems Research; vol. 55, Jun. 2019, pp. 60-76.
Jalali et al., Temporal super-resolution of 2D/3D echocardiography using cubic B-spline interpolation, Biomedical Signal Processing and Control, 10 pages. vol. 58, Apr. 2020, 101868.
Jimenez et al., Blind extraction of fetal and maternal components from the abdominal electrocardiogram: An ICA implementation for low-dimensional recordings, Biomedical Signal Processing and Control, 14 pages. vol. 58, Apr. 2020, 101836.
Kanai et al., "The structural basis of interindividual differences in human behaviour and cognition" Nat Rev Neurosci. Apr. 2011; 12(4): 231-42. doi: 10.1038/nrn3000. Epub Mar. 16, 2011.
Kang et al., Accuracy improvement of quantification information using super-resolution with convolutional neural network for microscopy images, Biomedical Signal Processing and Control, 8 pages. vol. 58, Apr. 2020, 101846.
Karar et al., Optimal adaptive intuitionistic fuzzy logic control of anti-cancer drug delivery systems, Biomedical Signal Processing and Control, 11 pages. vol. 58, Apr. 2020, 101861.
Kassahun et al., The effect of preoperative patient-reported anxiety on morbidity and mortality outcomes in patients undergoing major general surgery, Sci Rep. Apr. 15, 2022;12(1):6312, 11 pages.
Kim et al., Transparently bridging semantic gap in CPU management for virtualized environments, Journal of Parallel and Distributed Computing, vol. 71, Issue 6, 2011, 16 pages.
Kirchberger et al., Harmonic Frequency Lowering: Effects on the Perception of Music Detail and Sound Quality, Trends Hear, 10 pages. Feb. 1, 2016; 20: 2331216515626131.
Koelsch et al., Predictive Processes and the Peculiar Case of Music, Trends Cogn Sci. Jan. 2019; 23(1): 63-77. doi: 10.1016/j.tics.2018.10.006. Epub Nov. 21, 2018.
Kyriacou et al., Biomedical Signal Processing and Control, doi: 10.1016/81746-8094(20)30064-1, 1 page.
Kuhlmann et al., Music Affects Rodents: A Systematic Review of Experimental Research, Front Behav Neurosci;. Dec. 14, 2018;12:301. doi: 10.3389/fnbeh.2018.00301.
Kumar et al., Near lossless image compression using parallel fractal texture identification, Biomedical Signal Processing and Control, 9 pages. vol. 58, Apr. 2020, 101862.
Kumar et al., Walsh code based numerical mapping method for the identification of protein coding regions in eukaryotes, Biomedical Signal Processing and Control, 11 pages. vol. 58, Apr. 2020, 101859.
Kumar et al., Stacked auto-encoders based visual features for speech/music classification, Expert Systems with Applications, 208, Dec. 2022, 118041, 16 pages.
Li et al., Robust brain causality network construction based on Bayesian multivariate autoregression, Biomedical Signal Processing and Control, 13 pages. vol. 58, Apr. 2020, 101864.
Lichtl et al., Music Therapy for Pain in Black and White Cancer Patients: A Retrospective Study, J Pain Symptom Manage. Nov. 2022; 64(5): 478-485. doi: 10.1016/j.jpainsymman.2022.07.007. Epub Jul. 20, 2022.
Liu et al., Breast tumors recognition based on edge feature extraction usingsupport vector machine, Biomedical Signal Processing and Control, 8 pages. vol. 58, Apr. 2020, 101825.
Ludena et al., Chapter One—On interpretations of quantum mechanics and a novel nonrepresentational framework, Advances in Quantum Academic Press, vol. 83, 2021, pp. 1-29.
Loui et al., White Matter Correlates of Musical Anhedonia: Implications for Evolution of Music, Front Psychol, 10 pages. Sep. 25, 2017; 8:1664. doi: 10.3389/fpsyg.2017.01664.
Malik et al., Stacked convolutional and recurrent neural networks for music emotion recognition, arXiv preprint arXiv: 1706.02292, Jun. 2017, 6 pages.
Manning et al., Fitness tracking reveals task-specific associations between memory, mental health, and physical activity, Sci Rep. Aug. 15, 2022;12(1):13822, 12 pages.
Mastrandrea et al., The unbalanced reorganization of weaker functional connections induces the altered brain network topology in schizophrenia, Sci Rep. Jul. 28, 2021;11(1):15400, 14 pages.
Medhat et al., Masked Conditional Neural Networks for sound classification, Applied Soft Computing; 17pages. vol. 90, May 2020, 106073.
Millet et al., Soundtrack design: The impact of music on visual attention and affective responses, Applied Ergonomics, vol. 93, 2021, 103301, 9 pages.
Mirarkolaei et al., Frame rate up-conversion in cardiac ultrasound, Biomedical Signal Processing and Control, 13 pages. vol. 58, Apr. 2020, 101863.
Mitra et al., Text classification: A least square support vector machine approach, Applied Soft Computing, vol. 7, Issue 3, 2007, pp. 908-914.
Mori et al., Characterization of multi-domain postoperative recovery trajectories after cardiac surgery using a digital platform, NPJ Digit Med. Dec. 24, 2022; 5(1): 192, 8 pages.
Mostafa et al., Recognition of Western style musical genres using machine learning techniques, Expert Systems with Applications, vol. 36, Issue 8, 2009, pp. 11378-11389.
Nayak et al., A deep stacked random vector functional link network autoencoder for diagnosis of brain abnormalities and breast cancer, Biomedical Signal Processing and Control. 11 pages. vol. 58, Apr. 2020, 101860.
Nguyen et al., A qualitative study on stress, coping strategies and feasibility of music intervention among women with cancer receiving chemotherapy during COVID-19 pandemic in Vietnam, Sci Rep. Jan. 11, 2023; 13(1): 542, 11 pages.
Nijjar et al., Randomized Trial of Mindfulness-Based Stress Reduction in Cardiac Patients Eligible for Cardiac Rehabilitation, Sci Rep. Dec. 5, 2019; 9(1): 18415, 11 pages.
Nozais et al., Functionnectome as a framework to analyse the contribution of brain circuits to fMRI, Commun Biol. Sep. 2, 2021; 4(1):1035, 12 pages.

(56) References Cited

OTHER PUBLICATIONS

Oricco et al., Intonational cues to speaker bias in questions and the role of language exposure, Journal of Pragmatics, vol. 200, Oct. 2022, pp. 242-266.

Pan et al., A closed-loop brain-machine interface framework design for motor rehabilitation, Biomedical Signal Processing and Control, 9 pages. vol. 58, Apr. 2020, 101877.

Piazzese et al., 3D right ventricular endocardium segmentation in cardiac magnetic resonance images by using a new inter-modality statistical shape modelling method, Biomedical Signal Processing and Control, 11 pages. vol. 58, Apr. 2020, 101866.

Pinho et al., Individual Brain Charting, a high-resolution fMRI dataset for cognitive mapping, Sci Data. Jun. 12, 2018; 5:180105, 15 pages.

Pizzoli et al., A meta-analysis on heart rate variability biofeedback and depressive symptoms, Sci Rep. Mar. 23, 2011; 11(1): 6650, 10 pages.

Pradhan et al., Investigating the effect of sound in horror clip on the cardiac electrophysiology of young adults using wavelet packet decomposition and machine learning classifiers, Biomedical Engineering Advances; 9 pages, vol. 3, Jun. 2022, 100037.

Pucejdl et al., Rijke Organ: Modeling and Control of Array of Rijke Tubes, IFAC-PapersOnLine, vol. 53, Issue 2, 2020, pp. 8866-8871.

Pupikova et al., Inter-individual differences in baseline dynamic functional connectivity are linked to cognitive aftereffects of tDCS, Sci Rep 12, 20754, Dec. 2022, 12 pages.

Quan, J. et al., Incorporating Interpersonal Synchronization Features for Automatic Emotion Recognition from Visual and Audio Data during Communication, Sensors (Basel). Aug. 6, 2021; 21(16): 5317,18 pages.

Ramani et al., Improved image processing techniques for optic disc segmentation in retinal fundus images, Biomedical Signal Processing and Control, 18 pages. vol. 58, Apr. 2020, 101832.

Rehman et al., Machine learning-assisted signature and heuristic-based detection of malwares in Android devices Computers & Electrical Engineering; vol. 69, Jul. 2018, pp. 828-841.

Ren et al., Effective connectivity of the anterior hippocampus predicts recollection confidence during natural memory retrieval, 10 pages. NatCommun. Nov. 19, 2018; 9(1): 4875. doi: 10.1038/s41467-018-07325-4.

Roman et al., Data representations for audio-to-score monophonic music transcription, Expert Systems with Applications; 10 pages. vol. 162, Dec. 30, 2020, 113769.

Rouault et al., Forming global estimates of self-performance from local confidence, Nat Commun, 11 pages. Mar. 8, 2019; 10(1):1141. doi: 10.1038/s41467-019-09075-3.

Sadeghi et al., Character encoding based on occurrence probability enhances the performance of SSVEP-based BCI spellers, Biomedical Signal Processing and Control, 6 pages. vol. 58, Apr. 2020, 101888.

Sakkal et al., Learning to rock: The role of prior experience and explicit instruction on learning and transfer in a music videogame Computers & Education; vol. 128, Jan. 2019, pp. 389-397.

Salminen et al., Dual n-back training improves functional connectivity of the right inferior frontal gyrus at rest, Sci Rep. Nov. 23, 2020; 10(1): 20379, 10 pages.

Schaal et al., The effects of a music intervention during port catheter placement on anxiety and stress, Sci Rep. Mar. 11, 2021;11(1):5807, 10 pages.

Shan et al., Semantic-aware short path adversarial training for cross-domain semantic segmentation, Neurocomputing, vol. 380, 2020, pp. 125-132.

Schrempf et al., A randomised pilot trial of virtual reality-based relaxation for enhancement of perioperative well-being, mood and quality of life, Sci Rep. Jul. 14, 2022; 12(1): 12067, 12 pages.

Shany et al., Surprise-related activation in the nucleus accumbens interacts with music-induced pleasantness, Soc Cogn Affect Neurosci. May 17, 2019; 14(4): 459-470. doi: 10.1093/scan/nsz019.

Sharma et al., Automated emotion recognition based on higher order statistics anddeep learning algorithm, Biomedical Signal Processing and Control, 10 pages. vol. 58, Apr. 2020, 101867.

Sharma et al., Automated focal EEG signal detection based on third order cumulant function, Biomedical Signal Processing and Control, 8 pages. vol. 58, Apr. 2020, 101856.

Song et al., A new method for muscular visual fatigue detection using electrooculogram, Biomedical Signal Processing and Contro,. 9 pages. vol. 58, Apr. 2020, 101865.

Spielberger, C.D. et al., STAIAD instrument, State-Trait Anxiety Inventory for Adults, Instrument and Scoring Key, Mind Garden, 1968, 13 pages.

Supriatna et al., Fibonacci numbers. A population dynamics perspective, Heliyon. 2019; (5)1: e01130, 17 pages. Published Jan. 28, 2019. doi: 10.1016/j.heliyon.2019.e01130.

Taghia et al., Uncovering hidden brain state dynamics that regulate performance and decision-making during cognition, NatCommun. Jun. 27, 2018; 9(1): 2505, 19 pages, doi: 10.1038/s41467-018-04723-6.

Talukdar et al., Adaptation of Common Spatial Patterns based on mental fatigue for motor-imagery BCI, Biomedical Signal Processing and Control, 10 pages. vol. 58, Apr. 2020, 101829.

Thakur et al., Spark and Rule-KNN based scalable machine learning framework for EEG deceit identification, Biomedical Signal Processing and Control, 7 pages. vol. 58, Apr. 2020, 101886.

Turner et al., Small sample sizes reduce the replicability of task-based fMRI studies, Commun Biol 1, 62, 2018, 10 pages.

Tuncer et al., Multileveled ternary pattern and iterative ReliefF based bird sound classification, Applied Acoustics; 13 pages. vol. 176, May 2021, 107866.

Tuncer et al., Surface EMG signal classification using ternary pattern and discrete wavelet transform based feature extraction for hand movement recognition, Biomedical Signal Processing and Control, 12 pages. vol. 58, Apr. 2020, 101872.

Vareka et al., Evaluation of convolutional neural networks using a large multi-subject P300 dataset, Biomedical Signal Processing and Control, 7 pages. vol. 58, Apr. 2020, 101837.

Varrecchia et al., Generalization of a wavelet-based algorithm to adaptively detect activation intervals in weak and noisy myoelectric signals, Biomedical Signal Processing and Control, 8 pages. vol. 58, Apr. 2020, 101838.

Van Der Walt et al., The NumPy Array: A Structure for Efficient Numerical Computation, in Computing in Science & Engineering, vol. 13, No. 2, pp. 22-30, Mar.-Apr. 2011.

Yu et al., Adaptive neural fault-tolerant control for a class of strict-feedback nonlinear systems with actuator and sensor faults, Neurocomputing, vol. 380, 2020, pp. 87-94.

Wallman-Jones et al., Acute physical-activity related increases in interoceptive ability are not enhanced with simultaneous interoceptive attention, Sci Rep 12, 15054, Sep. 2022, 14 pages.

Wang et al., A high-precision arrhythmia classification method based on dual fullyconnected neural network, Biomedical Signal Processing and Control, 12 pages. vol. 58, Apr. 2020, 101874.

Wang et al., Temporal-spatial-frequency depth extraction of brain-computerinterface based on mental tasks, Biomedical Signal Processing and Control, 13 pages. vol. 58, Apr. 2020, 101845.

Wang et al., Neurocognitive patterns dissociating semantic processing from executive control are linked to more detailed off-task mental time travel, Sci Rep 10, 11904, Jul. 2020, 14 pages.

Wang et al., A cross-domain hierarchical recurrent model for personalized session-based recommendations, Neurocomputing, vol. 380, 2020, pp. 271-284.

Weber et al., Involvement of the default mode network under varying levels of cognitive effort, Sci Rep. Apr. 15, 2022;12(1):6303, 9 pages.

Wieczorkowska, Analytics and Applications of Audio and Image Sensing Techniques, Sensors (Basel). Nov. 3, 2022; 22(21): 8443, 4 pages.

Yan et al., Quantum probability-inspired graph neural network for document representation and classification, Neurocomputing; vol. 445, Jul. 20, 2021, pp. 276-286.

(56) References Cited

OTHER PUBLICATIONS

Yang et al., Evolving control of human-exoskeleton system using Gaussian process with local model, Biomedical Signal Processing and Control, 9 pages. vol. 58, Apr. 2020, 101844.

Yeh et al., Segment-based emotion recognition from continuous Mandarin Chinese speech, Computers in Human Behavior, vol. 27, Issue 5, Sep. 2011, pp. 1545-1552.

Zhang et al., A Kalman filtering based adaptive threshold algorithm for QRS complex detection, Biomedical Signal Processing and Control, 8 pages. vol. 58, Apr. 2020, 101827.

Zhang et al., Cerebrovascular segmentation from TOF-MRA using model- and data-driven method via sparse labels, Neurocomputing, vol. 380, 2020, pp. 162-179.

Zheng et al., Personalized modeling of pressure recognition based on Heart Rate Variability, Table 1, Proceedings of the 2018 8th International Conference on Manufacturing Science and Engineering, Atlantis Press, 2018, 1 page.

Zhou et al., Semantic graph construction for 3D geospatial data of multi-versions, Optik, vol. 125, Issue 6, 2014, pp. 1730-1734.

Zuber et al., Additive and interaction effects of working memory and motor sequence training on brain functional connectivity, Sci Rep. Nov. 29, 2021; 11(1): 23089, 12 pages.

Appleby et al., Preliminary Psychometric Validation of the Teammate Burnout Questionnaire, Front. Psychol., Aug. 1, 2022, Sec. Movement Science and Sport Psychology, vol. 13, 2022; https://doi.org/10.3389/fpsyg.2022.894308, 10 pages.

Asli et al., Model Gender Interacts With Expressed Emotion to Enhance Startle: Angry Male and Happy Female Faces Produce the Greatest Potentiation, Front. Hum. Neurosci., Nov. 9, 2020, Sec. Cognitive Neuroscience, vol. 14, 2020; https://doi.org/10.3389/fnhum.2020.576544, 8 pages.

Berrios, What Is Complex/Emotional About Emotional Complexity?, Front. Psychol., Jul. 12, 2019, Sec. Emotion Science, vol. 10, 2019; https://doi.org/10.3389/fpsyg.2019.01606, 11 pages.

Bao et al., Data Augmentation for EEG-Based Emotion Recognition Using Generative Adversarial Networks, Front. Comput. Neurosci., Dec. 9, 2021, vol. 15, 2021; https://doi.org/10.3389/fncom.2021.723843, 13 pages.

Cao et al., Multi-Source and Multi-Representation Adaptation for Cross-Domain Electroencephalography Emotion Recognition, Front. Psychol., Jan. 13, 2022, Sec. Emotion Science, vol. 12, 2021; https://doi.org/10.3389/fpsyg.2021.809459, 10 pages.

Chen et al., Sparse Granger Causality Analysis Model Based on Sensors Correlation for Emotion Recognition Classification in Electroencephalography, Front. Comput. Neurosci., Jul. 29, 2021, vol. 15, 2021; https://doi.org/10.3389/fncom.2021.684373, 12 pages.

Chung et al., Development and Validation of the Yonsei Face Database (YFace DB), Front. Psychol., Dec. 3, 2019, Sec. Emotion Science, vol. 10, 2019; https://doi.org/10.3389/fpsyg.2019.02626, 18 pages.

Coll et al., Emotional Intelligence, Empathy, Self-Esteem, and Life Satisfaction in Spanish Adolescents: Regression vs. QCA Models, Front. Psychol., Jul. 17, 2020, Sec. Educational Psychology, vol. 11, 2020; https://doi.org/10.3389/fpsyg.2020.01629, 10 pages.

DelVecchio et al., Anorexia and attachment: dysregulated defense and pathological mourning, Front. Psychol., Oct. 28, 2014, Sec. Psychology for Clinical Settings, vol. 5, 2014; https://doi.org/10.3389/fpsyg.2014.01218, 8 pages.

Esposito et al., Axiom, Anguish, and Amazement: How Autistic traits Modulae Emotional Mental Imagery, Front. Psychol., May 30, 2016, Sec. Emotion Science, vol. 7, 2016; https://doi.org/10.3389/fpsyg.2016.00757, 9 pages.

Fassbinder et al., Emotion Regulation in Schema Therapy and Dialectical Behavior Therapy, Front. Psychol., Sep. 14, 2016, Sec. Emotion Science, vol. 7, 2016; https://doi.org/10.3389/fpsyg.2016.01373, 19 pages.

Fischer et al., A Primer to (Cross-Cultural Multi-Group Invariance testing Possiblities in R, Front. Psychol., Jul. 18, 2019, Sec. Cultural Psychology, vol. 10, 2019; https://doi.org/10.3389/fpsyg.2019.01507, 18 pages.

Fraser et al., "Music Has No. Borders": An Exploratory Study of Audience Engagement With YouTube Music Broadcasts During COVID-19 Lockdown, 2020, Front. Psychol., Jul. 8, 2021, Sec. Cultural Psychology, vol. 12, 2021; https://doi.org/10.3389/fpsyg.2021.643893; 17 pages.

Garrido et al., KDEF-PT: Valence, Emotional Intensity, Familiarity and Attractiveness Ratings of Angry, Neutral, and Happy Faces, Front. Psychol., Dec. 19, 2017, Sec. Quantitative Psychology and Measurement, vol. 8, 2017; https://doi.org/10.3389/fpsyg.2017.02181, 9 pages.

Grecucci et al., Editorial: Advances in Emotion Regulation: From Neuroscience to Psychotherapy, Front. Psychol., Jun. 21, 2017, Sec. Emotion Science, vol. 8, 2017; https://doi.org/10.3389/fpsyg.2017.00985, 4 pages.

Gu et al., An Integrative Way for Studying Neural Basis of Basic Emotions With fMRI, Front. Neurosci., Jun. 19, 2019, Sec. Brain Imaging Methods, vol. 13, 2019; https://doi.org/10.3389/fnins.2019.00628, 12 pages.

Han et al., Using SPM 12's Second-Level Bayesian Inference Procedure for fMRI Analysis: Practical Guidelines for End Users, Front. Neuroinform., Feb. 2, 2018, vol. 12, 2018; https://doi.org/10.3389/fninf.2018.00001, 17 pages.

Han et al., Attainable and Relevant Moral Exemplars Are More Effective than Extraordinary Exemplars in Promoting Voluntary Service Engagement, Front. Psychol., Mar. 7, 2017, Sec. Educational Psychology, vol. 8, 2017; https://doi.org/10.3389/fpsyg.2017.00283, 14 pages.

Hayes et al., Emotion and cognition interactions in PTSD: a review of neurocognitive and neuroimaging studies, Front. Integr. Neurosci., Oct. 9, 2012, vol. 6, 2012; https://doi.org/10.3389/fnint.2012.00089, 14 pages.

Iyengar et al., Unresolved trauma in mothers: intergenerational effects and the role of reorganization, Front. Psychol., Sep. 1, 2014, Sec. Psychology for Clinical Settings, vol. 5, 2014; https://doi.org/10.3389/fpsyg.2014.00966, 9 pages.

Jami et al., Do Histories of Painful Life Experiences Affect the Expression of Empathy Among Young Adults? An Electroencephalography Study, Front. Psychol., Jul. 16, 2021, Sec. Emotion Science, vol. 12, 2021; https://doi.org/10.3389/fpsyg.2021.689304, 16 pages.

Jiang et al. Emotion Recognition Using Electroencephalography Signals of Older People for Reminiscence Therapy, Front. Physiol., Jan. 7, 2022, Sec. Physio-logging, vol. 12, 2021; https://doi.org/10.3389/fphys.2021.823013, 13 pages.

Jin et al., An Integrated Model of Emotional Problems, Beta Power of Electroencephalography, and Low Frequency of Heart Rate Variability after Childhood Trauma in a Non-Clinical Sample: A Path Analysis Study, Front. Psychiatry, Jan. 22, 2018, Sec. Mood Disorders, vol. 8, 2017; https://doi.org/10.3389/fpsyt.2017.00314, 9 pages.

Kuo et al., Using deep learning to study emotional behavior in rodent models, Front. Behav. Neurosci., Nov. 22, 2022, Sec. Emotion Regulation and Processing, vol. 16, 2022; https://doi.org/10.3389/fnbeh.2022.1044492, 9 pages.

Lacomba-Trejo et al., Psychosocial Factors and Chronic Illness as Predictors for Anxiety and Depression in Adolescence, Front. Psychol., Sep. 18, 2020, Sec. Educational Psychology, vol. 11, 2020; https://doi.org/10.3389/fpsyg.2020.568941, 9 pages.

LaRocque et al., Multiple neural states of representation in short-term memory? It's a matter of attention, Front. Hum. Neurosci., Jan. 23, 2014, Sec. Cognitive Neuroscience, vol. 8, 2014; https://doi.org/10.3389/fnhum.2014.00005, 14 pages.

Levstek, "It All Makes US Feel Together": Young People's Experiences of Virtual Group Music-Making During the COVID-19 Pandemic, Front. Psychol., Aug. 5, 2021, Sec. Cultural Psychology, vol. 12, 2021; https://doi.org/10.3389/fpsyg.2021.703892, 18 pages.

Li et al., Music aesthetic teaching and emotional visualization under emotional teaching theory and deep learning, Front. Psychol., Jul. 14, 2022, Sec. Educational Psychology, vol. 13, 2022; https://doi.org/10.3389/fpsyg.2022.911885, 15 pages.

(56) References Cited

OTHER PUBLICATIONS

Lichtenfeld et al., The Influence of Decisional and Emotional Forgiveness on Attributions, Front. Psychol., Jun. 25, 2019, Sec. Health Psychology, vol. 10, 2019; https://doi.org/10.3389/fpsyg.2019.01425, 8 pages.

Luo, Follow the heart or the head? The interactive influence model of emotion and cognition, Front. Psychol., May 6, 2015, Sec. Cognition, vol. 6, 2015; https://doi.org/10.3389/fpsyg.2015.00573, 14 pages.

Mattson et al., All Happy Emotions Are Alike but Every Unhappy Emotion Is Unhappy in Its Own Way: A Network Perspective to Academic Emotions, Front. Psychol., Apr. 30, 2020, Sec. Educational Psychology, vol. 11, 2020; https://doi.org/10.3389/fpsyg.2020.00742, 18 pages.

Olderbak et al., An emotion-differentiated perspective on empathy with the emotion specific empathy questionnaire, Front. Psychol., Jul. 1, 2014, Sec. Personality and Social Psychology, vol. 5, 2014; https://doi.org/10.3389/fpsyg.2014.00653, 14 pages.

Pardede et al., Revisiting the "The Breakfast Club": Testing Different Theoretical Models of Belongingness and Acceptance (and Social Self-Representation), Front. Psychol., Jan. 18, 2021, Sec. Personality and Social Psychology, vol. 11, 2020; https://doi.org/10.3389/fpsyg.2020.604090, 12 pages.

Rice, Commentary: The Neural Bases of Emotion Regulation, Front. Psychol., Mar. 31, 2016 Sec. Emotion Science, vol. 7, 2016; https://doi.org/10.3389/fpsyg.2016.00476, 3 pages.

Rohr et al., How Emotion Relates to Language and Cognition, Seen Through the Lens of Evaluative Priming Paradigms, Front. Psychol., Jul. 7, 2022, Sec. Language Sciences, vol. 13, 2022; https://doi.org/10.3389/fpsyg.2022.911068, 16 pages.

Romeo et al., Comparison of Slides and Video Clips as Different Methods for Inducing Emotions: An Electroencephalographic Alpha Modulation Study, Front. Hum. Neurosci., Jun. 6, 2022, Sec. Cognitive Neuroscience, vol. 16, 2022; https://doi.org/10.3389/fnhum.2022.901422, 12 pages.

Ross et al., Expanding Simulation Models of Emotional Understanding: The Case for Different Modalities, Body-State Simulation Prominence, and Developmental Trajectories, Front. Psychol., Mar. 3, 2020, Sec. Emotion Science, vol. 11, 2020; https://doi.org/10.3389/fpsyg.2020.00309; 21 pages.

Russo et al., Predicting musically induced emotions from physiological inputs: linear and neural network models, Front. Psychol., Aug. 8, 2013, Sec. Emotion Science, vol. 4, 2013; https://doi.org/10.3389/fpsyg.2013.00468, 8 pages.

Rosso et al., Ability Emotional Intelligence, Attachment Models, and Reflective Functioning, Front. Psychol., May 2, 2022, Sec. Psychology for Clinical Settings, vol. 13, 2022; https://doi.org/10.3389/fpsyg.2022.864446, 8 pages.

Schore, Early interpersonal neurobiological assessment of attachment and autistic spectrum disorders, Front. Psychol., Sep. 23, 2014, Sec. Psychology for Clinical Settings, vol. 5, 2014; https://doi.org/10.3389/fpsyg.2014.01049, 13 pages.

Shafir, Using Movement to Regulate Emotion: Neurophysiological Findings and Their Application in Psychotherapy, Front. Psychol., Sep. 23, 2016, Sec. Emotion Science, vol. 7, 2016; https://doi.org/10.3389/fpsyg.2016.01451, 6 pages.

Steinhubl et al., Cardiovascular and nervous system changes during meditation, Front. Hum. Neurosci., Mar. 18, 2015, Sec. Cognitive Neuroscience, vol. 9, 2015; https://doi.org/10.3389/fnhum.2015.00145, 10 pages.

Tao et al., The Impact of Parent-Child Attachment on Self-Injury Behavior: Negative Emotion and Emotional Coping Style as Serial Mediators, Front. Psychol., Jul. 31, 2020, Sec. Developmental Psychology, vol. 11, 2020; https://doi.org/10.3389/fpsyg.2020.01477; 10 pages.

Urizar et al., A Hierarchical Bayesian Model for Crowd Emotions, Front. Comput. Neurosci., Jul. 8, 2016, vol. 10, 2016; https://doi.org/10.3389/fncom.2016.00063, 9 pages.

Vempala et al., Modeling Music Emotion Judgments Using Machine Learning Methods, Front. Psychol., Jan. 5, 2018, Sec. Cognition, vol. 8, 2017; https://doi.org/10.3389/fpsyg.2017.02239; 12 pages.

Vissers et al., Theory of Mind Deficits and Social Emotional Functioning in Preschoolers with Specific Language Impairment, Front. Psychol., Nov. 4, 2016, Sec. Developmental Psychology, vol. 7, 2016; https://doi.org/10.3389/fpsyg.2016.01734; 7 pages.

Von Scheve, C., Emotion regulation and emotion work: two sides of the same coin?, Front. Psychol., Nov. 16, 2012, Sec. Emotion Science, vol. 3, 2012; https://doi.org/10.3389/fpsyg.2012.00496, 10 pages.

Wang et al., Emotion Recognition Algorithm Application Financial Development and Economic Growth Status and Development Trend, Front. Psychol., Feb. 28, 2022, Sec. Human-Media Interaction, vol. 13, 2022; https://doi.org/10.3389/fpsyg.2022.856409, 11 pages.

Wu et al., Applying Control-Value Theory and Unified Theory of Acceptance and use of Technology to Explore Pre-service Teachers' Academic Emotions and Learning Satisfaction, Front. Psychol., Nov. 8, 2021, Sec. Educational Psychology, vol. 12, 2021; https://doi.org/10.3389/fpsyg.2021.738959, 13 pages.

Zhang, Assessing Two Dimensions of Interpersonal Trust: Other-Focused Trust and Propensity to Trust, Front. Psychol., Jul. 27, 2021, Sec. Personality and Social Psychology, vol. 12, 2021; https://doi.org/10.3389/fpsyg.2021.654735, 11 pages.

Acharya et al., "An enhanced fitness function to recognize unbalanced human emotions data" Expert Systems with Application (2021) 166:114011, 14 pages.

Al et al., "Toward quantum teleporting living objects" Sci. Bull. (2016) 61(2):110-111, 2 pages.

Albott et al., "Battle Buddies: Rapid Deployment of a Psychological Resilience Intervention for Health Care Workers During the Coronavirus Disease 2019 Pandemic" Anesth Analg. Jul. 2020; 131(1):43-54. doi: 10.1213/ANE.0000000000004912. 12 pages.

Bach et al. "New Undersampling Method Based on the kNN Approach" Procedia Computer Science (2022) 207:3397-3406, 10 pages.

Balban et al., Brief structured respiration practices enhance mood and reduce physiological arousal, Cell Rep Med. Jan. 17, 2023; 4(1):100895. doi: 10.1016/j.xcrm.2022.100895. Epub Jan. 10, 2023. 2 pages.

Bansal et al., "Environmental Sound Classification: A descriptive review of the literature" Intelligent Systems with Applications (2022) 16:200115, 10 pages.

Barkana et al., "A new pitch-range based feature set for a speaker's age and gender classification" Applied Acoustics (2015) 98:52-61, 10 pages.

Cameron, Visceral brain-body information transfer, NeuroImage (2009) 47:787-794, 8 pages.

Cardoso et al., Intersection Explorer, a multi-perspective approach for exploring recommendations, International Journal of Human-Computer Studies (2019) 121:73-92, 20 pages.

Cechetto et al., Functional neuroanatomy of autonomic regulation, NeuroImage (2009) 47:795-803, 9 pages.

Chowanda et al., "Exploring deep learning algorithm to model emotions recognition from speech" Procedia Computer Science (2023) 216:706-713, 8 pages.

ClinicalTrials.gov PRS, "Pilot Study: The Effects of Medical Music on Anxiety in Patients With Interstitial Lung Disease" Unique Protocol ID: 1901019911, Jul. 2019, 4 pages.

Dasdemir et al., "Classification of Emotion Primitives from EEG Signals Using Visual and Audio Stimuli" IEEE, 2015 23nd Signal Processing and Communications Applications Conference (SIU), Malatya, Turkey, 2015, pp. 2250-2253, doi: 10.1109/SIU.2015.7130325. 4 pages.

Deng et al., Erythrocytes No. in healthy individuals and anaemia laminar blood flow in the Ulnar vein in both men and women: The analysis of multi-phase heat transfer for medical application, Alexandria Engineering Journal (2022) 61:10099-10107, 9 pages.

Desolda et al., Exploring spatially-aware cross-device interaction techniques for mobile collaborative sensemaking, International Journal of Human-Computer Studies (2019) 122:1-20, 20 pages.

(56) References Cited

OTHER PUBLICATIONS

Dogan et al., "A novel ternary and signum kernelled linear hexadecimal pattern and hybrid feature selection based environmental sound classification method" Measurement (2020) 166:108151, 10 pages.
Drossos et al., "Affective Audio Synthesis for Sound Experience Enhancement", Experimental Multimedia Systems for Interactivity and Strategic Inovation, I. Deliyannis, P. Kostagiolas (Eds), IGI-Global, 2016, pp. 1-20.
Eddin et al., Femtomolar detection of dopamine using surface plasmon resonance sensor based on chitosan/graphene quantum dots thin film. Spectrochimica Acta Part A: Molecular and Biomolecular Spectroscopy (2021) 263:120202, 10 pages.
Eduardo et al., Biomass feeding in cellulosic ethanol projects: An underestimated issue? Alexandria Engineering Journal (2022) 61:10233-10244, 12 pages.
Elugoke et al., Electrochemical sensor for the detection of dopamine using carbon quantum dots/copper oxide nanocomposite modified electrode, FlatChem (2022) 33:100372, 13 pages.
Farajzadeh et al., PMG-Net: Persian music genre classification using deep neural networks, Entertainment Computing (2023) 44:100518, 12 pages.
Farzan et al., Following others through an information maze: The impact of social navigation on information seeking behavior, International Journal of Human-Computer Studies (2019) 124:81-92, 12 pages.
Fotiou et al., Exploiting caching, proxy re-encryption, incentives, and Wi-Fi Direct for authorized content distribution, Procedia Computer Science (2016) 98:80-86, 7 pages.
Gao et al., "EEG emotion recognition based on enhanced SPD matrix and manifold dimensionality reduction" Computers in Biology and Medicine (2022) 146:105606, 12 pages.
Garcia-Pedrajas et al., Cooperative coevolutionary instance selection for multilabel problems, Knowledge-Based Systems (2021) 234:107569, 17 pages.
Gendolla et al., (eds.), "Handbook of Biobehavioral Approaches to Self-Regulation" Springer, New York (2015) 413 pages.
Ghatas et al., A hybrid deep learning approach for musical difficulty estimation of piano symbolic music, Alexandria Engineering Journal (2022) 61:10183-10196, 14 pages.
Guggari et al., "Music rhythm tree based partitioning approach to decision tree classifier" Journal of King Saud University—Computer and Information Sciences (2022) 34:3040-3054, 15 pages.
"Harmonyze, Harness the Power of Music" by Neural+, a Jacobs-Cornell Technion Institute Runway Company, 12 pages.
He et al., "Strengthen EEG-based emotion recognition using firefly integrated optimization algorithm" Applied Soft Computing Journal (2020) 94:106426, 17 pages.
Hizlisoy et al., Music emotion recognition using convolutional long short term memory deep neural networks, Engineering Science and Technology, an International Journal (2021) 24:760-767, 8 pages.
Hossain et al., Observers' physiological measures in response to videos can be used to detect genuine smiles, International Journal of Human-Computer Studies (2019) 122:232-241, 10 pages.
Houssaini et al., A Novel Reaction Scheme against the MAC Layer Misbehavior in Mobile Ad Hoc Networks, Procedia Computer Science (2016) 98:64-71, 8 pages.
Hua et al., "Deep Belief Networks and deep learning" Proceedings of 2015 International Conference on Intelligent Computing and Internet of Things, DOI: 10.1109/ICAIOT.2015.7111524 Corpus ID: 2754701, 5 pages.
Idrobo-Avila et al., Can the application of certain music information retrieval methods contribute to the machine learning classification of electrocardiographic signals? Heliyon (2021) 7:e06257, 10 pages.
Jabeur et al., A Firefly-Inspired Micro and Macro Clustering Approach for Wireless Sensor Networks, Procedia Computer Science (2016) 98:132-139, 8 pages.
Karydis et al., Comparing content and context based similarity for musical data, Neurocomputing (2013) 107:69-76, 8 pages.
Kim et al., "Polysomnographic phenotyping of obstructive sleep apnea and its implications in mortality in Korea" Sci Rep. Aug. 6, 2020; 10(1):13207. doi: 10.1038/s41598-020-70039-5. 12 pages.
Konaka, "Design of Discrete Predictive Controller Using Approximate Nearest Neighbor Method" IFAC Proceedings Volumes (2011) 44(1):10213-10218, 6 pages.
Kulkarni et al., Context Aware Recommendation Systems: A review of the state of the art techniques, Computer Science Review (2020) 37:100255, 33 pages.
Kumar et al., Dynamic popularity window and distance-based efficient caching for fast content delivery applications in CCN, Engineering Science and Technology, an International Journal (2021) 24:829-837, 9 pages.
Lai et al., A social recommendation method based on the integration of social relationship and product popularity, International Journal of Human-Computer Studies (2019) 121:42-57, 16 pages.
Le et al., UIFGAN: An unsupervised continual-learning generative adversarial network for unified image fusion, Information Fusion (2022) 88:305-318, 14 pages.
Li et al., RFN-Nest: An end-to-end residual fusion network for infrared and visible Images, Information Fusion (2021) 73:72-86, 15 pages.
Li et al., Effects of thermal processing on N,N-dimethylpiperidinium (mepiquat) formation in meat and vegetable products, Food Research International (2021) 150:110771, 7 pages.
Li et al., Dynamic early warning of rockburst using microseismic multi-parameters based on Bayesian network, Engineering Science and Technology, an International Journal (2021) 24:715-727.
Liang et al., "A hybrid quantum-classical neural network with deep residual" Neural Networks (2021) 1443:133-147, 15 pages.
Lima et al., "Variable selection for inferential models with relatively high-dimensional data: Between method heterogeneity and covariate stability as adjuncts to robust selection" Sci Rep. May 14, 2020; 10(1):8002. doi: 10.1038/S41598-020-64829-0. 11 pages.
Liu et al., Reducing biogenic amine in seriflux and huangjiu by recycling of seriflux inoculated with Lactobacillus plantarum JN01, Food Research International (2021) 150:110793, 9 pages.
Liu et al., Real-time social recommendation based on graph embedding and temporal context, International Journal of Human-Computer Studies (2019) 121:58-72, 15 pages.
Liu et al., "Functional connectivity of major depression disorder using ongoing EEG during music perception" Clinical Neurophysiology (2020) 131:2413-2422, 10 pages.
Macy et al., Circumplex Model of Affect and Motivational State, BIOPAC Systems, Inc., Jan. 12, 2016, 6 pages.
Metzig et al., Classification of origin with feature selection and network construction for folk tunes, Pattern Recognition Letters (2020) 133:356-364, 9 pages.
Mukherjee et al., ComposeInStyle: Music composition with and without Style Transfer, Expert Systems with Applications (2022) 191:116195, 21 pages.
Mustaqeem et al., MLT-DNet: Speech emotion recognition using 1D dilated CNN based on multi-learning trick approach, Expert Systems With Applications (2021) 167:114177, 12 pages.
Musto et al., Linked open data-based explanations for transparent recommender systems, International Journal of Human-Computer Studies (2019) 121:93-107, 15 pages.
Nie, "Disperse and preserve the perverse: computing how hip-hop censorship changed popular music genres in China" Poetics (2021) 88:101590, 16 pages.
No author provided, Table of Contents, Heart and Lung, Sep./Oct. vol. 44, No. 5, 3 pages.
No author provided, Information for Readers, Heart and Lung, 2015, 44, 5, 1 page.
Pandya et al., Ambient acoustic event assistive framework for identification, detection, and recognition of unknown acoustic events of a residence, Advanced Engineering Infomatics (2021),47:101238, 21 pages.
Peperkamp et al., "Broadening the perspective on how to recognize emotion in music" Delft University of Technology, The Netherlands, 2105, 7 pages.

(56) References Cited

OTHER PUBLICATIONS

Radford et al., Learning Transferable Visual Models From Natural Language Supervision, arXiv:2103.00020v1, Feb. 26, 2021, https://doi.org/10.48550/arXiv.2103.00020, 48 pages.
Rastin et al., A generalized weighted distance k-Nearest Neighbor for multi-label problems, Pattern Recogniton (2021) 114:107526, 16 pages.
Redeker et al., Information for Authors, Heart & Lung, Sep./Oct. 2015, vol. 44, No. 5, 3 pages.
Sakalle et al., A LSTM based deep learning network for recognizing emotions using wireless brainwave driven system, Expert Systems with Applications (2021) 173:114516, 19 pages.
Salcuni, (ed.), "Frontiers Research Topics: Attachment Assessment in Treatments, Prevention and Intervention Programs" Frontiers in Psychology, Apr. 2015, 105 pages.
Sanchez-Moreno et al., A collaborative filtering method for music recommendation using playing coefficients for artists and users, Expert Systems With Applications (2016) 66:234-244, 11 pages.
Santos et al., "Enriching teachers' assessments of rhythmic Forró dance skills by modelling motion sensor data" International Journal of Human—Computer Studies (2022) 161:102776, 14 pages.
Sanz-Cruzado et al., "Effective contact recommendation in social networks by adaptation of information retrieval models" Information Processing and Management (2020) 57:102285, 25 pages.
Santiago et al. The emerging healthcare professional: Certified yoga therapist (C-IAYT). Complement Ther Clin Pract. May 2020; 39:101147. doi: 10.1016/j.ctcp.2020.101147. Epub Mar. 18, 2020.
Shakhovska et al., "Data analysis of music preferences of web users based on social and demographic factors" Procedia Computer Science (2022) 198:730-735, 6 pages.
Sharma et al., Categorization of ICMR Using Feature Extraction Strategy and MIR with Ensemble Learning, Procedia Computer Science (2015) 57:686-694, 9 pages.
Shahamirifard et al., A simple ultrasensitive electrochemical sensor for simultaneous determination of gallic acid and uric acid in human urine and fruit juices based on zirconia-choline chloride-gold nanoparticlesmodified carbon paste electrode, Biosens Bioelectron. Aug. 30, 2018; 114:30-36. doi: 10.1016/j.bios.2018.05.009. Epub May 8, 2018. 7 pages.
Singh et al., Robustness of musical features on deep learning models for music genre classification, Expert Systems With Applications (2022) 199:116879, 14 pages.
Song et al., A Survey of Music Recommendation Systems and Future Perspectives, 9th International Symposium on Computer Music Modelling and Retrieval (CMMR 2012) Jun. 19-22, 2012, Queen Mary University of London, 395-410, 16 pages.
Trstenjak et al., "KNN with TF-IDF Based Framework for Text Categorization" Procedia Engineering (2014) 69:1356-1364, 9 pages.
Toiviainen et al., "Measuring and modeling real-time responses to music: The dynamics of tonality induction" Perception (2003) vol. 32, pp. 741-766, 26 pages.
Tsalera et al., Monitoring, profiling and classification of urban environmental noise using sound characteristics and the KNN algorithm, Energy Reports (2020) 6:223-230, 8 pages.
Uddin et al., Stokes' second problem and oscillatory Couette flow for a two-layer fluid: Analytical solutions, Alexandria Engineering Journal (2022) 61:10197-10218, 22 pages.
Vibhute et al., "Fluorescent carbon quantum dots: Synthesis methods, functionalization and biomedical applications" Applied Surface Science Advances (2022) 11:100311, 16 pages.
Warren et al., Improving comprehension of knowledge representation languages: A case study with Description Logics, International Journal of Human-Computer Studies (2019) 122:145-167, 23 pages.
Wang et al., Hierarchically Stacked Graph Convolution for emotion recognition in conversation, Knowledge-Based Systems (2023), doi: https://doi.org/10.1016/j.knosys.2023.110285. 14 pages.
Wang et al., "Review of the emotional feature extraction and classification using EEG signals" Cognitive Robotics (2021) 1:29-40, 12 pages.
Yang et al.,"A novel graphene quantum dots/choline chloride/gold nanoparticlesmodified carbon fiber microelectrode for sensitive and selective determination of dopamine in the presence of a high concentration of ascorbic acid" Journal of Electroanalytical Chemistry (2021) 895:115512, 7 pages.
Yin et al., "A careful assessment of recommendation algorithms related to dimension reduction techniques" Knowledge-Based Systems (2012) 27:407-423,17 pages.
Zhang et al., "Deep Emotional Arousal Network for Multimodal Sentiment Analysis and Emotion Recognition" Information Fusion (2022) 88:296-304, 9 pages.
Zimmermann et al., "Temporal Context affects interval timing at the perceptual level" Sci Rep. May 29, 2020; 10(1):8767. doi: 10.1038/s41598-020-65609-6. 10 pages.
Allen et al., A massive 7T fMRI dataset to bridge cognitive neuroscience and artificial intelligence, Nat Neurosci 25, 116-126 (2022). https://doi.org/10.1038/s41593-021-00962-x.
Anwani et al., Training multi-layer spiking neural networks using NormAD based spatio-temporal error backpropagation, Neurocomputing 380, 2020, 67-77; Epub Nov. 6, 2019.
Boreland et al., The effectiveness of tight glycemic control on decreasing surgical site infections and readmission rates in adult patients with diabetes undergoing cardiac surgery: A systematic review. Heart Lung. Sep.-Oct. 2015;44(5): 430-40. doi: 10.1016/j.hrtlng.2015.06.004. Epub Jun. 29, 2015.
Boukhris et al., Reply to "Effect of cardiac rehabilitation on ventricular repolarization in patients with type 2 diabetes and coronary heart disease: Non-invasive quantification via transmural dispersion of repolarization". Heart Lung. Sep.-Oct. 2015 44(5): 461. doi: 10.1016/j.hrtlng.2015.05.007. Epub Jun. 16, 2015, p. 461.
Cai et al., Dynamic causal brain circuits during working memory and their functional controllability. Nat Commun 12, 3314(2021), 16 pages; https://doi.org/10.1038/s41467-021-23509-x.
Cabrera et al., Bayesian approach and time series dimensionality reduction to LSTM-based model-building for fault diagnosis of a reciprocating compressor. Neurocomputing. Mar. 7, 2020; 380: 51-66. Epub Nov. 8, 2019.
Chen et al., Implementation of circuit for reconfigurable memristive chaotic neural network and its application in associative memory. Neurocomputing. Mar. 7, 2020; 380: 36-42. Epub Nov. 5, 2019.
Chen et al., Efficacy and safety of moxibustion for chronic low back pain: A systematic review and meta-analysis of randomized controlled trials. Complement Ther Clin Pract. May 2020; 39:101130. doi: 10.1016/j.ctcp.2020.101130. Epub Feb. 29, 2020, 10 pages.
Correll, J., A discretely adaptive connection logic network. Neurocomputing. Mar. 7, 2020; 380: 285-305. Epub Nov. 6, 2019.
Dashtipour, et al., A hybrid Persian sentiment analysis framework: Integrating dependency grammar based rules and deep neural networks. Neurocomputing. Mar. 7, 2020; 380:1-10. Epub Oct. 17, 2019.
da Silva et al., Iatrogenic pneumothorax in mechanically ventilated children: Incidence, risk factors and other outcomes. Heart Lung. May-Jun. 2015; 44(3): 238-42. doi: 10.1016/j.hrtlng.2015.01.005. Epub Feb. 11, 2015.
da Silva et al. Reply to "Iatrogenic pneumothorax: What can we do?" Heart & Lung, Letter to the Editor, vol. 44, Issue 5, Sep. 2015, pp. 458-459, https://doi.org/10.1016/j.hrtlng.2015.01.005.
de Schotten et al., Brain disconnections link structural connectivity with function and behaviour, Nat Commun 11, 5094 (2020). https://doi.org/10.1038/s41467-020-18920-9, 8 pages.
Derbis et al., Short antisense oligonucleotides alleviate the pleiotropic toxicity of RNA harboring expanded CGG repeats, Nat Commun 12, 1265 (2021), 17 pages; https://doi.org/10.1038/s41467-021-21021-w.
Ding et al., Multi-scale fully convolutional network for gland segmentation using three-class classification. Neurocomputing. Mar. 7, 2020; 380: 150-61. Epub Nov. 5, 2019.
Dolev et al., Physiological parameters of mental health predict the emergence of post-traumatic stress symptoms in physicians treating COVID-19 patients, Translational Psychiatry (2021) 11:169, 9 pages.
Doorley et al., Positive and Negative Emotion Regulation in College Athletes: A Preliminary Exploration of Daily Savoring, Accep-

(56) References Cited

OTHER PUBLICATIONS tance, and Cognitive Reappraisal, Cognit Ther Res. 2021;45(4):598-613. doi: 10.1007/s10608-020-10202-4. Epub Jan. 22, 2021.

Eerola et al., Modeling Listeners' Emotional Response to Music, Topics in Cognitive Science (2012) 1-18; DOI: 10.1111/j.1756-8765.2012.01188.x.

Eerola et al., Modeling Emotional Effects of Music: Key Areas of Improvement, Proceedings of Sound and Music Computing Conference 2013, SMC 2013, Stockholm, Sweden, 8 pages.

Emami et al., Vitamin D suppresses proangiogenic factors in patients with ulcerative colitis: A randomized double blind placebo controlled clinical trial. Complement Ther Clin Pract. May 2020; 39:101086. doi: 10.1016/j.ctcp.2020.101086. Epub Jan. 7, 2020. PMID: 31957666, 5 pages.

Feder et al., Physicians' perceptions of the Thrombolysis in Myocardial Infarction (TIMI) risk score in older adults with acute myocardial infarction. Heart Lung. Sep.-Oct. 2015; 44(5): 376-81. doi: 10.1016/j.hrtlng.2015.05.005. Epub Jul. 9, 2015.

Fu et al., A two-stage attention aware method for train bearing shed oil inspection based on convolutional neural networks. Neurocomputing. Mar. 7, 2020; 380: 212-24. Epub Nov. 9, 2019.

Gao et al., A GPSO-optimized convolutional neural networks for EEG-based emotion recognition. Neurocomputing. Mar. 7, 2020; 380: 225-35. Epub Nov. 5, 2019.

Garrido-Merchán, et al., Dealing with categorical and integer-valued variables in Bayesian Optimization with Gaussian processes. Neurocomputing. Mar. 7, 2020; 380: 20-35. Epub Nov. 9, 2019.

Grant et al., Clinician response time for positive blood culture results in a pediatric ICU. Heart Lung. Sep.-Oct. 2015; 44(5): 426-9. doi: 10.1016/j.hrtlng.2015.06.003. Epub Jul. 11, 2015.

Han et al., Power scheduling optimization under single-valued neutrosophic uncertainty, Neurocomputing, vol. 382, 2020, pp. 12-20, https://doi.org/10.1016/j.neucom.2019.11.089.

Happ et al., Quality of care and resource use among mechanically ventilated patients before and after an intervention to assist nurse-nonvocal patient communication. Heart Lung. Sep.-Oct. 2015; 44(5):408-415.e2. doi: 10.1016/j.hrtlng.2015.07.001. Erratum in: Heart Lung. Nov. 2015-Dec. 44(6): 546. Paull, Brooke [corrected to Baumann, Brooke M].

He et al., C9orf72 functions in the nucleus to regulate DNA damage repair cell, Cell Death Differ. Oct. 11, 2022. doi: 10.1038/s41418-022-01074-0, 15 pages.

Hetland, et al., The influence of music during mechanical ventilation and weaning from mechanical ventilation: A review. Heart Lung. Sep.-Oct. 2015;44(5): 416-25. doi: 10.1016/j.hrtlng.2015.06.010. Epub Jul. 27, 2015.

Khan et al., Enriching Non-negative Matrix Factorization with Contextual Embeddings for Recommender Systems. Neurocomputing. Mar. 7, 2020; 380: 246-58. Epub Oct. 2, 2019.

Kim et al. High school baseball players' experiences with static qigong training: A qualitative approach. Complement Ther Clin Pract. May 2020; 39:101158. doi: 10.1016/j.ctcp.2020.101158. Epub Apr. 13, 2020, 8 pages.

Kim et al., Changes to information in working memory depend on distinct removal operations, Nat Commun 11, 6239 (2020). https://doi.org/10.1038/s41467-020-20085-4, 14 pages.

Kodama et al., Reversal of diffuse patchy pattern in lung perfusion scan in a case of severe pulmonary arterial hypertension. Heart Lung. Sep.-Oct. 2015; 44(5): 451-2. doi: 10.1016/j.hrtlng.2015.06.005. Epub Jun. 29, 2015.

Kommineni et al., Advances in computer-human interaction for detecting facial expression using dual tree multi band wavelet transform and Gaussian mixture model, Neural Computing and Applications (2022) 34:15397-15408.

Landi et al., Relationship between cardiovascular health metrics and physical performance in community-living people: Results from the Longevity check-up (Lookup) 7+ project, Scientific Reports 2018, 8:16353; DOI:10.1038/s41598-018-34746-4, 8 pages.

LaRocque et al., Decoding Attended Information in Short-term Memory: An EEG Study, J Cgn Neurosci. Jan. 2013, 25(1):127-142; doi:10.1162/jocn_a_00305.

Li et al., Containment control with multiple leaders for nonlinear multi-agent systems with unstabilizable linearizations. Neurocomputing. Mar. 7, 2020; 380: 43-50. Epub Nov. 4, 2019.

Lim et al., MFC: Initialization method for multi-label feature selection based on conditional mutual information, Neurocomputing, vol. 382, 2020, pp. 40-51, https://doi.org/10.1016/j.neucom.2019.11.071.

Lim et al., Discordant attributes of structural and functional brain connectivity in a two-layer multiplex network, Sci Rep 9, 2885 (2019). https://doi.org/10.1038/s41598-019-39243-w, 13 pages.

Lin et al., Quaternion broad learning system: A novel multi-dimensional filter for estimation and elimination tremor in teleoperation. Neurocomputing. Mar. 7, 2020; 380: 78-86. Epub Oct. 28, 2019.

Lin et al., A novel deep neural network based approach for sparse code multiple access. Neurocomputing. Mar. 21, 2020; 382: 52-63.

Liu et al., Exploring privileged information from simple actions for complex action recognition. Neurocomputing. Mar. 7, 2020;380:236-45. Epub Nov. 13, 2019.

Liu et al., Intelligent online catastrophe assessment and preventive control via a stacked denoising autoencoder. Neurocomputing. Mar. 7, 2020; 380: 306-20. Epub Nov. 15, 2019.

Luo et al., Local manifold sparse model for image classification, Neurocomputing, vol. 382, 2020, pp. 162-173, https://doi.org/10.1016/j.neucom.2019.11.084.

Ma et al., Discriminative deep metric learning for asymmetric discrete hashing. Neurocomputing. Mar. 7, 2020; 380: 115-24. Epub Nov. 8, 2019.

Ma et al., PCFNet: Deep neural network with predefined convolutional filters. Neurocomputing. Mar. 21, 2020; 382: 32-9.

Malm et al., Pulmonary artery dissection in a patient with undiagnosed pulmonary hypertension—A case report and review of literature. Heart Lung. Sep.-Oct. 2015; 44(5): 453-7. doi: 10.1016/j.hrtlng.2015.06.006. Epub Jul. 4, 2015.

McDonald et al., A closer look: Alternative pain management practices by heart failure patients with chronic pain. Heart Lung. Sep.-Oct. 2015; 44(5): 395-9. doi: 10.1016/j.hrtlng.2015.06.001. Epub Jun. 16, 2015.

Mancuso et al., The homotopic connectivity of the functional brain: a meta-analytic approach, Sci Rep 9, 3346 (2019). https://doi.org/10.1038/s41598-019-40188-3, 19 pages.

Mann et al., MeCP2 Controls an Epigenetic Pathway That Promotes Myofibroblast Transdifferentiation and Fibrosis, Gastroenterology 2010, 138:705-714.

Martin et al., Inspecting adversarial examples using the fisher information, Neurocomputing, vol. 382, 2020, pp. 80-86, https://doi.org/10.1016/j.neucom.2019.11.052.

Mendoca, et al. Comments on "Effects of auriculotherapy on weight and body mass index reduction in patients with overweight or obesity: Systematic review and meta-analysis". Complement Ther Clin Pract. May 2020; 39:101123. doi: 10.1016/j.ctcp.2020.101123. Epub Feb. 24, 2020, 3 pages.

Music Therapy for the Cancer Patient, Course Description, Memorial Sloan Kettering Cancer Center, Sep. 25, 2019, https://www.mskcc.org/departments/survivorship-supportive-care/integrative-medicine/programs/music-therapy, 6 pages.

Nakai et al., Quantitative models reveal the organization of diverse cognitive functions in the brain, Nat Commun. Mar. 2, 2020; 11(1):1142. doi: 10.1038/s41467-020-14913-w, 12 pages.

Narasimhan et al., The Nature of the Heisenberg-von Neumann Cut: Enhanced Orthodox Interpretation of Quantum Mechanics, Activas Nervosa Superior 2019, 61:12-17.

Pan et al., Annealed gradient descent for deep learning. Neurocomputing. Mar. 7, 2020; 380: 201-11. Epub Nov. 13, 2019.

Patron et al., The impact of COVID-19-related quarantine on psychological outcomes in patients after cardiac intervention: a multicenter longitudinal study, Transl Psychiatry. Jun. 6, 2022;12(1):235. doi: 10.1038/s41398-022-01984-0, 9 pages.

(56) References Cited

OTHER PUBLICATIONS

Perez et al. The emerging healthcare professional: Certified yoga therapist (C-IAYT). Complement Ther Clin Pract. May 2020; 39: 101147. doi: 10.1016/j.ctcp.2020.101147. Epub Mar. 18, 2020, 8 pages.
Prasun New heart failure treatment and nursing care. Heart Lung. Sep. 2015-Oct. 44(5): 367. doi: 10.1016/j.hrtlng.2015.07.004. Epub Aug. 1, 2015, 1 page.
Ren et al., Data-based stable value iteration optimal control for unknown discrete-time systems with time delays. Neurocomputing. Mar. 21, 2020; 382: 96-105.
Rosenfeld et al., Symptom clusters in patients presenting to the emergency department with possible acute coronary syndrome differ by sex, age, and discharge diagnosis. Heart Lung. Sep.-Oct. 2015; 44(5): 368-75. doi: 10.1016/j.hrtlng.2015.05.008. Epub Jun. 26, 2015.
Saleh et al., Decreasing sedentary behavior by 30 minutes per day reduces cardiovascular disease risk factors in rural Americans. Heart Lung. Sep.-Oct. 2015; 44(5): 382-6. doi: 10.1016/j.hrtlng.2015.06.008. Epub Jul. 27, 2015.
Shan et al., Semantic-aware short path adversarial training for cross-domain semantic segmentation. Neurocomputing. Mar. 7, 2020; 380:125-32. Epub Nov. 9, 2019.
Shi et al., Optimizing zinc electrowinning processes with current switching via Deep Deterministic Policy Gradient learning. Neurocomputing. Mar. 7, 2020 ;380:190-200. Epub Nov. 13, 2019.
Shibata et al., Small molecule targeting r(UGGAA)n disrupts RNA foci and alleviates disease phenotype in Drosophila model, Nat Commun 12, 236 (2021). https://doi.org/10.1038/s41467-020-20487-4, 13 pages.
Sitaram et al., Closed-loop brain training: the science of neurofeedback, Nat Rev Neurosci 18, 86-100 (2017). https://doi.org/10.1038/nrn.2016.164.
Soubani et al., The outcome of acute respiratory distress syndrome in relation to body mass index and diabetes mellitus. Heart Lung. Sep.-Oct. 2015; 44(5): 441-7. doi: 10.1016/j.hrtlng.2015.06.007. Epub Jul. 23, 2015.
Sun et al., Quantized synchronization of memristive neural networks with time-varying delays via super-twisting algorithm. Epub Nov. 12, 2019. Neurocomputing. Mar. 7, 2020; 380: 133-40.
Sunkara et al., Left ventricular pseudoaneurysm as a fatal complication of purulent pericarditis, Heart & Lung, vol. 44, Issue 5, 2015, pp. 448-450, https://doi.Org/10.1016/j.hrtlng.2015.06.002.
Teng et al., Delay tolerant containment control for second-order multi-agent systems based on communication topology design. Neurocomputing. Mar. 7, 2020; 380:11-9. Epub Oct. 21, 2019.
Thompson et al., 'Music and Emotion: Psychological Considerations', in Elisabeth Schellekens, and Peter Goldie (eds), The Aesthetic Mind: Philosophy and Psychology (Oxford, 2011; online edn, Oxford Academic, Jan. 19, 2012), https://doi.org/10.1093/acprof:oso/9780199691517.003.0022, 19 pages.
Tokatli et al., Effect of cardiac rehabilitation on ventricular repolarization in patients with type 2 diabetes and coronary heart disease: Non-invasive quantification via transmural dispersion of repolarization. Heart Lung. Sep.-Oct. 2015; 44(5): 459-60. doi: 10.1016/j.hrtlng.2015.05.006. Epub Jun. 8, 2015.
Tuncer et al., LEDPatNet19: Automated Emotion Recognition Model based on Nonlinear LED Pattern Feature Extraction Function using EEG Signals, Cogn Neurodyn 16, 779-790 (2022). https://doi.org/10.1007/s11571-021-09748-0.
Vatansever et al., Varying demands for cognitive control reveals shared neural processes supporting semantic and episodic memory retrieval. Nat Commun 12, 2134 (2021), 11 pages; https://doi.org/10.1038/S41467-021-22443-2.
Wang et al., A cross-domain hierarchical recurrent model for personalized session-based recommendations. Neurocomputing. Mar. 7, 2020; 380: 271-84. Epub Nov. 13, 2019.
Wang et al., Adversarial attacks on faster r-cnn object detector. Neurocomputing, Mar. 2, 20201; 382: 87-95.
Wang et al., Multi-scale multi-patch person re-identification with exclusivity regularized softmax, Neurocomputing, vol. 382, 2020, pp. 64-70, https://doi.org/10.1016/j.neucom.2019.11.062.
Wang et al., Individual-specific functional connectivity markers track dimensional and categorical features of psychotic illness, Mol Psychiatry 25, 2119-2129 (2020). https://doi.org/10.1038/s41380-018-0276-1.
Weninger et al., On the Acoustics of Emotion in Audio: What Speech, Music, and Sound have in Common, Front Psychol. May 27, 2013;4:292. doi: 10.3389/fpsyg.2013.00292. eCollection 2013, 12 pages.
Xie et al., Multi-view clustering by joint manifold learning and tensor nuclear norm. Neurocomputing. Mar. 7, 2020; 380:105-14. Epub Nov. 13, 2019.
Xie et al., Performance of the Automated Neuropsychological Assessment Metrics (ANAM) in detecting cognitive impairment in heart failure patients. Heart Lung. Sep.-Oct. 2015; 44(5): 387-94. doi: 10.1016/j.hrtlng.2015.07.002.
Xue et al., Frame-GAN: Increasing the frame rate of gait videos with generative adversarial networks. Neurocomputing. Mar. 7, 2020; 380: 95-104. Epub Nov. 13, 2019.
Xue et al., Wavelet-based residual attention network for image super-resolution. Neurocomputing. Mar. 21, 2020; 382:116-26.
Yang et al., Prediction of the Distribution of Perceived Music Emotions Using Discrete Samples, in IEEE Transactions on Audio, Speech, and Language Processing, vol. 19, No. 7, pp. 2184-2196, Sep. 2011, doi: 10.1109/TASL.2011.2118752.
Yang et al., Ranking-Based Emotion Recognition for Music Organization and Retrieval, in IEEE Transactions on Audio, Speech, and Language Processing, vol. 19, No. 4, pp. 762-774, May 2011, doi: 10.1109/TASL.2010.2064164.
Yang et al., Quantitative Study of Music Listening Behavior in a Social and Affective Context, IEEE Transactions on Multimedia 15(6):1304-1315.
You et al., Impaired dynamic functional brain properties and their relationship to symptoms in never treated first-episode patients with schizophrenia. Schizophr 8, 90 (2022), 9 pages; https://doi.org/10.1038/s41537-022-00299-9.
Yu et al., Adaptive neural fault-tolerant control for a class of strict-feedback nonlinear systems with actuator and sensor faults. Neurocomputing. Mar. 7, 2020; 380: 87-94. Epub Oct. 10, 2019.
Yu et al., Relative-output-based consensus for nonlinear multi-agent systems with unknown measurement sensitivities, Neurocomputing, vol. 382, 2020, pp. 21-31, https://doi.org/10.1016/j.neucom.2019.11.082.
Yu et al., A health education booklet and telephone follow-ups can improve medication adherence, health-related quality of life, and psychological status of patients with heart failure. Heart Lung. Sep.-Oct. 2015; 44(5): 400-7. doi: 10.1016/j.hrtlng.2015.05.004. Epub Jun. 6, 2015.
Zhang et al., Cerebrovascular segmentation from TOF-MRA using model- and data-driven method via sparse labels. Neurocomputing. Mar. 7, 2020; 380: 162-79. Epub Nov. 6, 2019.
Zhang et al., Feature agglomeration networks for single stage face detection. Neurocomputing. Mar. 7, 2020; 380:180-9. Epub Nov. 4, 2019.
Zhang et al., Network representation learning with ensemble methods. Neurocomputing. Mar. 7, 2020; 380: 141-9. Epub Nov. 5, 2019.
Zhang et al., A low-cost and high-speed hardware implementation of spiking neural network, Neurocomputing, vol. 382, 2020, pp. 106-115; https://doi.org/10.1016/j.neucom.2019.11.045.
Zhao et al., A visual long-short-term memory based integrated CNN model for fabric defect image classification. Neurocomputing. Mar. 7, 2020; 380: 259-70. Epub Nov. 11, 2019.
Zhang et al., CascadeGAN: A category-supervised cascading generative adversarial network for clothes translation from the human body to tiled images. Neurocomputing. Mar. 21, 2020; 382:148-61.
Zhong, et al., DNA computing inspired deep networks design. Neurocomputing. Mar. 21, 2020; 382:140-7.
Zhou et al., Decentralized composite suboptimal control for a class of two-time-scale interconnected networks with unknown slow dynamics, Neurocomputing, vol. 382, 2020, pp. 71-79, https://doi.org/10.1016/j.neucom.2019.11.057.

(56) References Cited

OTHER PUBLICATIONS

Zovetti et al., Inefficient white matter activity in Schizophrenia evoked during intra and inter-hemispheric communication, Transl Psychiatry 12, 449 (2022). https://doi.org/10.1038/s41398-022-02200-9, 11 pages.
Zwilling et al., Enhanced decision-making through multimodal training, npj Sci. Learn. 4, 11 (2019), 10 pages; https://doi.org/10.1038/s41539-019-0049-x.
Aczel, et al. Discussion points for Bayesian inference. Nat Hum Behav. Jun. 2020; 4(6): 561-563. doi: 10.1038/s41562-019-0807-z.
Álvarez, D et al. A machine learning-based test for adult sleep apnoea screening at home using oximetry and airflow. Sci Rep. Mar. 24, 2020; 10(1): 5332. doi: 10.1038/s41598-020-62223-4, 12 pages.
Amlien, IK et al. Elaboration Benefits Source Memory Encoding Through Centrality Change. Sci Rep. Mar. 6, 2019; 9(1): 3704. doi: 10.1038/s41598-019-39999-1, 13 pages.
Anderson, AJ et al. Decoding individual identity from brain activity elicited in imagining common experiences. NatCommun. Nov. 20, 2020; 11(1): 5916. doi: 10.1038/s41467-020-19630-y, 14 pages.
Arnulfo G et al. Long-range phase synchronization of high-frequency oscillations in human cortex. Nat Commun. Oct. 23, 2020;11(1):5363. doi: 10.1038/s41467-020-18975-8, 15 pages.
Assaneo, et al. Speaking rhythmically can shape hearing. Nat Hum Behav. Jan. 2021; 5(1): 71-82. doi: 10.1038/S41562-020-00962-0. Epub Oct. 12, 2020.
Assaneo, MF et al. Spontaneous synchronization to speech reveals neural mechanisms facilitating language learning. Nat Neurosci. Apr. 2019; 22(4): 627-632. doi: 10.1038/s41593-019-0353-z. Epub Mar. 4, 2019.
Bartley, JE et al. Brain activity links performance in science reasoning with conceptual approach. NPJ Sci Learn. Dec. 2, 2019; 4: 20. doi: 10.1038/s41539-019-0059-8, 8 pages.
Bellana, B et al. Narrative thinking lingers in spontaneous thought. Nat Commun. Aug. 6, 2022; 13(1): 4585. doi: 10.1038/S41467-022-32113-6, 16 pages.
Bohn, M et al. How young children integrate information sources to infer the meaning of words. Nat Hum Behav. Aug. 2021; 5(8): 1046-1054. doi: 10.1038/s41562-021-01145-1. Epub Jul. 1, 2021.
Bolt, T et al. A parsimonious description of global functional brain organization in three spatiotemporal patterns. Nat Neurosci. Aug. 2022; 25(8): 1093-1103. doi: 10.1038/s41593-022-01118-1. Epub Jul. 28, 2022.
Boundy-Singer, ZM et al. Confidence reflects a noisy decision reliability estimate. Nat Hum Behav. Jan. 2023; 7(1): 142-154. doi: 10.1038/s41562-022-01464-x. Epub Nov. 7, 2022.
Cetron, J.S. et al. Decoding individual differences in STEM learning from functional MRI data. Nat Commun 10, 2027, May 2, 2019. https://doi.org/10.1038/s41467-019-10053-y, 10 pages.
Chen, Oy et al. Resting-state brain information flow predicts cognitive flexibility in humans. Sci Rep. Mar. 7, 2019; 9(1): 3879. doi: 10.1038/s41598-019-40345-8, 16 pages.
Choi, W et al. Intrinsic timescales of sensory integration for motion perception. Sci Rep. Mar. 8, 2019; 9(1): 3993. doi: 10.1038/s41598-019-40649-9, 15 pages.
Coffey, E.B.J. et al. Evolving perspectives on the sources of the frequency-following response. Nat Commun 10, 5036, Nov. 6, 2019. https://doi.org/10.1038/s41467-019-13003-w, 10 pages.
Cox, C et al. A systematic review and Bayesian meta-analysis of the acoustic features of infant-directed speech. Nat Hum Behav. Jan. 2023; 7(1): 114-133. doi: 10.1038/s41562-022-01452-1. Epub Oct. 3, 2022.
Daly, I. et al. Neural and physiological data from participants listening to affective music. Sci Data 7,177 (2020). https://doi.org/10.1038/s41597-020-0507-6, 7 pages.
de Vries, SEJ et al. A large-scale standardized physiological survey reveals functional organization of the mouse visual cortex. Nat Neurosci. Jan. 2020; 23(1): 138-151. doi: 10.1038/s41593-019-0550-9. Epub Dec. 16, 2019.

Desender, K et al. Dynamic influences on static measures of metacognition. Nat Commun. Jul. 21, 2022; 13(1): 4208. doi: 10.1038/s41467-022-31727-0, 12 pages.
DRISSI—DAOUDI L et al. Feature integration within discrete time windows. NatCommun. Oct. 25, 2019; 10(1):4901. doi: 10.1038/s41467-019-12919-7, 8 pages.
Elmer, S et al. Theta Coherence Asymmetry in the Dorsal Stream of Musicians Facilitates Word Learning. Sci Rep. Mar. 15, 2018; 8(1): 4565. doi: 10.1038/s41598-018-22942-1, 13 pages.
Fornaciai, M et al. Modality-specific temporal constraints for state-dependent interval timing. Sci Rep 8, 10043 (2018). https://doi.org/10.1038/s41598-018-28258-4, 10 pages.
Fornaciai, M et al. Motion-induced compression of perceived numerosity. Sci Rep. May 3, 2018; 8(1): 6966. doi: 10.1038/541598-018-25244-8, 11 pages.
Franci, A et al. Deep neural network models of sound localization reveal how perception is adapted to real-world environments. Nat Hum Behav. Jan. 2022; 6(1): 111-133. doi: 10.1038/s41562-021-01244-z. Epub Jan. 27, 2022.
Gelding, R.W. et al. Musical imagery depends upon coordination of auditory and sensorimotor brain activity. Sci Rep 9, 16823 (2019). https://doi.org/10.1038/s41598-019-53260-9, 13 pages.
Gu, S et al. The Energy Landscape of Neurophysiological Activity Implicit in Brain Network Structure. Sci Rep. Feb. 6, 2018; 8(1):2507. doi: 10.1038/s41598-018-20123-8, 15 pages.
Hahn, G et al. Portraits of communication in neuronal networks. Nat Rev Neurosci. Feb. 2019; 20(2): 117-127. doi: 10.1038/s41583-018-0094-0.
Han, X et al. Diversity of spatiotemporal coding reveals specialized visual processing streams in the mouse cortex. NatCommun 13, 3249 (2022). https://doi.org/10.1038/s41467-022-29656-z, 18 pages.
Henaff, OJ et al. Primary visual cortex straightens natural video trajectories. Nat Commun. Oct. 13, 2021; 12(1):5982. doi: 10.1038/s41467-021-25939-z, 12 pages.
Heron, J et al. Adaptation reveals multi-stage coding of visual duration. Sci Rep. Feb. 28, 2019; 9(1): 3016. doi: 10.1038/S41598-018-37614-3, 11 pages.
Hills, et al. Filling gaps in early word learning. Nat Hum Behav. Sep. 2018; 2(9):622-623. doi: 10.1038/s41562-018-0428-y.
Himmelberg, MM et al. Linking individual differences in human primary visual cortex to contrast sensitivity around the visual field. NatCommun. Jun. 13, 2022; 13(1): 3309. doi: 10.1038/s41467-022-31041-9, 13 pages.
Iyer, KK et al. Focal neural perturbations reshape low-dimensional trajectories of brain activity supporting cognitive performance. NatCommun. Jan. 10, 2022; 13(1): 4. doi: 10.1038/s41467-021-26978-2, 8 pages.
Jasmin, K et al. Understanding rostral-caudal auditory cortex contributions to auditory perception. Nat Rev Neurosci. Jul. 2019; 20(7): 425-434. doi: 10.1038/s41583-019-0160-2.
Ju, H et al. Dynamic representations in networked neural systems. Nat Neurosci. Aug. 2020; 23(8): 908-917. doi: 10.1038/S41593-020-0653-3. Epub Jun. 15, 2020.
Kelly, et al. Neurocomputational mechanisms of prior-informed perceptual decision-making in humans. Nat Hum Behav 5, 467-481 (2021). https://doi.org/10.1038/s41562-020-00967-9.
Keung W et al. A divisive model of evidence accumulation explains uneven weighting of evidence over time. NatCommun. May 1, 2020; 11(1): 2160. doi: 10.1038/s41467-020-15630-0, 9 pages.
Kong, X et al. Sensory-motor cortices shape functional connectivity dynamics in the human brain. Nat Commun. Nov. 4, 2021; 12(1): 6373. doi: 10.1038/s41467-021-26704-y, 15 pages.
Kruschke, JK. Bayesian Analysis Reporting Guidelines. Nat Hum Behav. Oct. 2021; 5(10): 1282-1291. doi: 10.1038/S41562-021-01177-7. Epub Aug. 16, 2021.
Legaspi R et al. A Bayesian psychophysics model of sense of agency. Nat Commun. Sep. 18, 2019; 10(1): 4250. doi: 10.1038/s41467-019-12170-0, 11 pages.
Lisi, M et al. Discrete confidence levels revealed by sequential decisions. Nat Hum Behav 5, 273-280 (2021). https://doi.org/10.1038/s41562-020-00953-1.
Lohuis, MNO, Pie JL, Marchesi P, Montijn JS, de Kock CPJ, Pennartz CMA, Olcese U. Author Correction: Multisensory task

(56) References Cited

OTHER PUBLICATIONS demands temporally extend the causal requirement for visual cortex in perception. Nat Commun. Jul. 14, 2022; 13(1): 4088. doi: 10.1038/s41467-022-31518-7, 19 pages.

Madsen, J et al. Music synchronizes brainwaves across listeners with strong effects of repetition, familiarity and training. Sci Rep 9, 3576 (2019). https://doi.org/10.1038/s41598-019-40254-w, 8 pages.

Maier, S.U et al. Dissociable mechanisms govern when and how strongly reward attributes affect decisions. Nat Hum Behav 4, 949-963 (2020). https://doi.org/10.1038/s41562-020-0893-y.

Marx V. Machine learning, practically speaking. Nat Methods. Jun. 2019; 16(6): 463-467. doi: 10.1038/s41592-019-0432-9.

Mason, et al. The neuroscience of advanced scientific concepts. NPJ Sci Learn. Oct. 11, 2021;6(1):29. doi: 10.1038/s41539-021-00107-6. Erratum in: NPJ Sci Learn. Dec. 8, 2021; 6(1): 37, 12 pages.

McPherson, T et al. Intrinsic Rhythmicity Predicts Synchronization-Continuation Entrainment Performance. Sci Rep. Aug. 6, 2018; 8(1): 11782. doi: 10.1038/s41598-018-29267-z, 14 pages.

Mehrpour V et al. Attention amplifies neural representations of changes in sensory input at the expense of perceptual accuracy. Nat Commun 11, 2128 (2020). https://doi.org/10.1038/s41467-020-15989-0, 8 pages.

Meshulam, M et al. Neural alignment predicts learning outcomes in students taking an introduction to computer science course. Nat Commun. Mar. 26, 2021; 12(1): 1922. doi: 10.1038/s41467-021-22202-3, 14 pages.

Muller, EJ, Munn BR, Shine JM. Diffuse neural coupling mediates complex network dynamics through the formation of quasi-critical brain states. Nat Commun. Dec. 10, 2020; 11(1): 6337. doi: 10.1038/s41467-020-19716-7, 11 pages.

Murai, Y et al. Optimal multisensory integration leads to optimal time estimation. Sci Rep. Aug. 30, 2018; 8(1): 13068. doi: 10.1038/s41598-018-31468-5, 11 pages.

Nigam, S et al. Adaptive coding across visual features during free-viewing and fixation conditions. Nat Commun 14, 87 (2023). https://doi.org/10.1038/s41467-022-35656-w, 12 pages.

Papini, GB et al. Estimation of the apnea-hypopnea index in a heterogeneous sleep-disordered population using optimised cardiovascular features. Sci Rep. Nov. 26, 2019; 9(1): 17448. doi: 10.1038/s41598-019-53403-y, 16 pages.

Parker, D.B. et al. Task-evoked Negative BOLD Response and Functional Connectivity in the Default Mode Network are Representative of Two Overlapping but Separate Neurophysiological Processes. Sci Rep 9, 14473 (2019). https://doi.org/10.1038/s41598-019-50483-8, 17 pages.

Pesnot J et al. Multisensory correlation computations in the human brain identified by a time-resolved encoding model. Nat Commun. May 5, 2022; 13(1): 2489. doi: 10.1038/s41467-022-29687-6, 12 pages.

Piasini, E. et al. Temporal stability of stimulus representation increases along rodent visual cortical hierarchies. Nat Commun 12, 4448 (2021). https://doi.org/10.1038/s41467-021-24456-3, 19 pages.

Poeppel, D et al. Speech rhythms and their neural foundations. Nat Rev Neurosci. Jun. 2020; 21(6): 322-334. doi: 10.1038/s41583-020-0304-4. Epub May 6, 2020.

Sankaran, N. et al. Decoding the dynamic representation of musical pitch from human brain activity. Sci Rep 8, 839 (2018). https://doi.org/10.1038/s41598-018-19222-3, 9 pages.

Schustek P, Hyafil A, Moreno-Bote R. Human confidence judgments reflect reliability-based hierarchical integration of contextual information. NatCommun. Nov. 28, 2019; 10(1): 5430. doi: 10.1038/s41467-019-13472-z, 15 pages.

Shine, JM et al. Human cognition involves the dynamic integration of neural activity and neuromodulatory systems. Nat Neurosci. Feb. 2019; 22(2): 289-296. doi: 10.1038/s41593-018-0312-0. Epub Jan. 21, 2019.

Sit, KK et al. Distributed and retinotopically asymmetric processing of coherent motion in mouse visual cortex. NatCommun. Jul. 16, 2020; 11(1): 3565. doi: 10.1038/s41467-020-17283-5, 14 pages.

Sizemore, AE et al. Knowledge gaps in the early growth of semantic feature networks. Nat Hum Behav. Sep. 2018;2(9):682-692. doi: 10.1038/s41562-018-0422-4. Epub Sep. 7, 2018.

Soreq, E. et al. Neuroimaging evidence for a network sampling theory of individual differences in human intelligence test performance. Nat Commun 12, 2072 (2021). https://doi.org/10.1038/s41467-021-22199-9, 13 pages.

Speed, A., Del Rosario, J., Mikail, N et al. Spatial attention enhances network, cellular and subthreshold responses in mouse visual cortex. Nat Commun 11, 505 (2020). https://doi.org/10.1038/s41467-020-14355-4, 11 pages.

Stawarczyk, D et al. The dynamics of memory retrieval for internal mentation. Sci Rep. Sep. 26, 2019; 9(1): 13927. doi: 10.1038/s41598-019-50439-y, 13 pages.

Stella, M. et al. Multiplex model of mental lexicon reveals explosive learning in humans. Sci Rep 8, 2259 (2018). https://doi.org/10.1038/s41598-018-20730-5, 11 pages.

Teixeira, Borges, A.F. et al. Scaling behaviour in music and cortical dynamics interplay to mediate music listening pleasure. Sci Rep 9, 17700 (2019). https://doi.org/10.1038/s41598-019-54060-x, 15 pages.

Teschendorf, AE. Avoiding common pitfalls in machine learning omic data science. Nat Mater. May 2019; 18(5): 422-427. doi: 10.1038/s41563-018-0241-z.

van der Heijden, K et al. Cortical mechanisms of spatial hearing. Nat Rev Neurosci. Oct. 2019; 20(10): 609-623. doi: 10.1038/s41583-019-0206-5. Epub Aug. 29, 2019.

Wagenmakers, EJ et al. Seven steps toward more transparency in statistical practice. Nat Hum Behav 5, 1473-1480 (2021). https://doi.org/10.1038/s41562-021-01211-8.

Wang, Y et al. Differential modulation of the auditory steady state response and inhibitory gating by chloral hydrate anesthesia. Sci Rep. Feb. 27, 2018; 8(1): 3683. doi: 10.1038/s41598-018-21920-x, 9 pages.

Wood KC et al. Neurons in primary auditory cortex represent sound source location in a cue-invariant manner. NatCommun. Jul. 9, 2019; 10(1):3019. doi: 10.1038/s41467-019-10868-9. PMID: 31289272; PMCID: PMC6616358, 15 pages.

Yeshurun, Y et al. The default mode network: where the idiosyncratic self meets the shared social world. Nat Rev Neurosci. Mar. 2021; 22(3): 181-192. doi: 10.1038/s41583-020-00420-w. Epub Jan. 22, 2021.

Zhang, N et al. Rhythmic pattern facilitates speech production: An ERP study. Sci Rep. Sep. 10, 2019; 9(1): 12974. doi: 10.1038/s41598-019-49375-8, 11 pages.

Accornero et al., A fracture mechanics approach to the design of hybrid-reinforced concrete beams, Engineering Fracture Mechanics (2022) 275:108821, 15 pages.

Abramsky et al., Possibilities determine the combinatorial structure of probability polytopes, Journal of Mathematical Psychology (2016) 74:58-65, 8 pages.

Aerts et al., From ambiguity aversion to a generalized expected utility. Modeling preferences in a quantum probabilistic framework, Journal of Mathematical Psychology (2016) 74:117-127, 11 pages.

Agrahari et al., Novel drug delivery systems: Emerging development opportunities and translational challenges European Journal of Pharmaceutics and Biopharmaceutics (2022) 179:182-183, 2 pages.

Al-Sarayreh et al., Software engineering principles: A systematic mapping study and a quantitative literature review, Engineering Science and Technology, an International Journal (2021) 24:768-781, 14 pages.

Anas et al., Optical properties of chitosan/hydroxyl-functionalized graphene quantum dots thin film for potential optical detection of ferric (III) ion, Optics and Laser Technology (2019) 120:10572, 8 pages.

Antoine et al., Graphene quantum dots as bimodal imaging agent for X-ray and Computed Tomography, European Journal of Pharmaceutics and Biopharmaceutics (2022) 179:74-78, 5 pages.

Asano et al., A quantum-like model of selection behavior, Journal of Mathematical Psychology (2017) 78:2-12, 11 pages.

Bartlett et al., Motion adaptation and attention: A critical review and meta-analysis, Neurosci Biobehav Rev. Jan. 2019; 96:290-301. doi: 10.1016/j.neubiorev.2018.10.010. Epub Oct. 22, 2018. 12 pages.

(56) References Cited

OTHER PUBLICATIONS

Caldwell et al., Fatigue and its management in the workplace, Neuroscience and Biobehavioral Reviews (2019) 96:272-289, 18 pages.

Calvo-Zaragoza et al., Improving kNN multi-label classification in Prototype Selection scenarios using class proposals, PatternRecognition (2015) 48:1608-1622, 15 pages.

Carvalho et al., A Role for The P2Y1 Receptor in Nonsynaptic Cross-depolarization in the Rat Dorsal Root Ganglia, Neuroscience. Dec. 15, 2019; 423:98-108. doi: 10.1016/j.neuroscience.2019.09.038. Epub Nov. 2, 2019. 11 pages.

Cersosimo et al., Central control of autonomic function and involvement in neurodegenerative disorders, Handb Clin Neurol. 2013;117:45-57. doi: 10.1016/B978-0-444-53491-0.00005-5, 13 pages.

Champagne et al., The perceived benefits of Dance Movement Therapy for parents of a child on the autism spectrum: A pilot study, The Arts in Psychotherapy (2022) 77:101875, 9 pages.

Colonius et al., An invitation to coupling and copulas: With applications to multisensory modeling, Journal of Mathematical Psychology (2016) 74:2-10, 9 pages.

Dekkers et al., A meta-analytical evaluation of the dual-hormone hypothesis: Does cortisol moderate the relationship between testosterone and status, dominance, risk taking, aggression, and psychopathy? Neurosci Biobehav Rev. Jan. 2019; 96:250-271. doi: 10.1016/j.neubiorev.2018.12.004. Epub Dec. 7, 2018. 22 pages.

De Witte et al., Development of a music therapy micro-intervention for stress reduction, The Arts in Psychotherapy (2022) 77:101872, 11 pages.

Diederich et al., Multi-stage sequential sampling models with finite or infinite time horizon and variable boundaries, Journal of Mathematical Psychology (2016) 74:128-145, 18 pages.

Dzhafarov et al., Context—content systems of random variables: The Contextuality-by-Default theory, Journal of Mathematical Psychology (2016) 74:11-33, 23 pages.

Drost et al., Repetitive negative thinking as a transdiagnostic factor in depression and anxiety: A conceptual replication, Behaviour Research and Therapy 63 (2014) 177-183, 7 pages.

Fayek et al., Evaluating deep learning architectures for Speech Emotion Recognition, Neural Networks (2017) 92:60-68, 9 pages.

Fischer et al., Polymorphisms in genes related to the hypothalamic-pituitary-adrenal axis and antidepressant response—Systematic review, Neurosci Biobehav Rev. Jan. 2019; 96:182-196. doi: 10.1016/j.neubiorev.2018.11.009. Epub Nov. 19, 2018. 15 pages.

Geipel et al., "Short-term music therapy treatment for adolescents with depression—A pilot study" The Arts in Psychotherapy (2022) 77:101874, 11 pages.

Gunji et al., Quantum cognition based on an ambiguous representation derivedfrom a rough set approximation, BioSystems (2016) 141:55-66, 12 pages.

Ha et al., Short-term heart rate variability in older patients with newly diagnosed depression, Psychiatry Res. Apr. 30, 2015; 226(2-3):484-8. doi: 10.1016/j.psychres.2015.02.005. Epub Feb. 20, 2015. 5 pages.

Hattori et al., "Association between dysfunction of autonomic nervous system activity and mortality in schizophrenia" Compr Psychiatry. Oct. 2018; 86:119-122. doi: 10.1016/j.comppsych.2018.08.002. Epub Aug 9, 2018. 4 pages.

Hongdan et al., An intelligent music genre analysis using feature extraction and classification using deep learning techniques, Computers and Electrical Engineering (2022) 100:107978, 17 pages.

Hosford et al., What is the key mediator of the neurovascular coupling response?, Neurosci Biobehav Rev. Jan. 2019; 96:174-181. doi: 10.1016/j.neubiorev.2018.11.011. Epub Nov. 24, 2018. 8 pages.

Inbar et al., "Sequences of Intonation Units form a~ 1 Hz rhythm" Sci Rep. Sep. 28, 2020; 10(1):15846. doi: 10.1038/s41598-020-72739-4. 9 pages.

Jia et al., Multi-dimensional classification via k NN feature augmentation, Pattern Recognition (2020) 106:107423, 11 pages.

Kemp et al., From psychological moments to mortality: A multi-disciplinary synthesis on heart rate variability spanning the continuum of time, Neurosci Biobehav Rev. Dec. 2017; 83:547-567. doi: 10.1016/j.neubiorev.2017.09.006. Epub Sep. 6, 2017. 21 pages.

Kumar et al., Wavelet based machine learning models for classification of human emotions using EEG signal, Measurement: Sensors (2022) 24:100554, 8 pages.

Li et al., Speech emotion recognition using recurrent neural networks with directional self-attention, Expert Systems With Applications (2021) 173:114683, 13 pages.

Liu et al., MGNN: A multiscale grouped convolutional neural network for efficient atrial fibrillation detection, Computers in Biology and Medicine Sep. 2022; 148:105863. doi: 10.1016/j.compbiomed.2022.105863. Epub Jul. 15, 2022. 11 pages.

Liu et al., Microstructure-based modelling of hydraulic fracturing in silicified metamorphic rock using the cohesive element method, Engineering Fracture Mechanics (2022) 276:108912, 18 pages.

Liu et al., An emotion-based personalized music recommendation framework for emotion improvement, Information Processing and Management (2023) 60:103256, 12 pages.

Matsuno, Biological computation running on quantum computation, BioSystems (2021) 207:104467, 5 pages.

Moon et al., "Meter enhances the subcortical processing of speech sounds at a strong beat" Sci Rep. Sep. 29, 2020; 10(1):15973. doi: 10.1038/s41598-020-72714-z, 8 pages.

Moreira et al., Exploring the relations between Quantum-Like Bayesian Networks and decision-making tasks with regard to face stimuli, Journal of Mathematical Psychology (2017) 78:86-95, 10 pages.

Morriss et al., The uncertain brain: A co-ordinate based meta-analysis of the neural signatures supporting uncertainty during different contexts, Neuroscience and Biobehavioral Reviews (2019) 96:241-249, 9 pages.

Mukhtar et al., Coupled multiphysics 3-D generalized finite element method simulations of hydraulic fracture propagation experiments, Engineering Fracture Mechanics (2022) 276:108874, 27 pages.

Ntalampiras et al., Speech emotion recognition via learning analogies, Pattern Recognition Letters (2021) 144:21-26, 6 pages.

Pothos et al., The dynamics of decision making when probabilities are vaguely specified, Journal of Mathematical Psychology (2014) 59:6-17, 12 pages.

Powers et al., Regulating emotion through distancing: A taxonomy, neurocognitive model, and supporting meta-analysis, Neurosci Biobehav Rev. Jan. 2019; 96:155-173. doi: 10.1016/j.neubiorev.2018.04.023. Epub Nov. 28, 2018. 19 pages.

Reznik et al., Motor output, neural states and auditory perception, Neurosci Biobehav Rev. Jan. 2019; 96:116-126. doi: 10.1016/j.neubiorev.2018.10.021. Epub Nov. 2, 2018. 11 pages.

Su et al., High-performance content-based music retrieval via automated navigation and semantic features, Engineering Applications of Artificial Intelligence (2022) 115:105267, 16 pages.

Sun et al., "Electrodeposition synthesis of a NiO/CNT/PEDOT composite forsimultaneous detection of dopamine, serotonin, and tryptophan" Sensors and Actuators B: Chemical (2018) 259:433-442, 10 pages.

Susini et al., "Auditory local—global temporal processing: evidence for perceptual reorganization with musical expertise" Sci Rep. Oct. 2, 2020; 10(1):16390. doi: 10.1038/s41598-020-72423-7. 12 pages.

Teasdale, (1983), Negative thinking in depression: Cause, effect, or reciprocal relationship?, Advances in Behaviour Research and Therapy, 5(1), 3-25, 23 pages, https://doi.org/10.1016/0146-6402(83)90013-9.

Teghil et al., Inter-individual differences in resting-state functional connectivity are linked to interval timing in irregular contexts, Cortex. Jul. 2020; 128:254-269. doi: 10.1016/j.cortex.2020.03.021. Epub Apr. 8, 2020. 16 pages.

Teghil et al., Neural substrates of internally-based and externally-cued timing: An activation likelihood estimation (ALE) meta-analysis of fMRI studies, Neurosci Biobehav Rev. Jan. 2019; 96:197-209. doi: 10.1016/j.neubiorev.2018.10.003. Epub Oct. 11, 2018. 13 pages.

(56) References Cited

OTHER PUBLICATIONS

Teixeira-Machado et al., Dance for neuroplasticity: A descriptive systematic review, Neurosci Biobehav Rev. Jan. 2019; 96:232-240. doi: 10.1016/j.neubiorev.2018.12.010. Epub Dec. 10, 2018. 9 pages.

Tiwara et al., "An ammonia sensor based on Lossy Mode Resonances on a taperedoptical fibre coated with porphyrin-incorporated titanium dioxide" Sensors and Actuators B: Chemical (2017) 242:645-652, 8 pages.

Vatansever et al., Developmental alterations of the numerical processing networks in the brain, Brain and Cognition (2020) 141:105551, 9 pages.

Verma et al., A flexible piezoelectric generator based on KNN/PVDF composite films: Role of KNN concentration on the piezoelectric performance of generator, Chinese Journal of Physics (2022), doi: https://doi.org/10.1016/j.cjph.2022.12.007, 35 pages.

Vetter et al., Prospective study of chronotype and incident depression among middle- and older-aged women in the Nurses' Health Study II, J Psychiatr Res. Aug. 2018; 103:156-160. doi: 10.1016/j.jpsychires.2018.05.022. Epub May 25, 2018. 5 pages.

Vicario et al., A systematic review on the therapeutic effectiveness of non-invasive brain stimulation for the treatment of anxiety disorders, Neurosci Biobehav Rev . Jan. 2019; 96:219-231. doi: 10.1016/j.neubiorev.2018.12.012. Epub Dec. 10, 2018. 13 pages.

Wang et al., Systems biology and gene networks in Alzheimer's disease, Neurosci Biobehav Rev. Jan. 2019; 96:31-44. doi: 10.1016/j.neubiorev.2018.11.007. Epub Nov. 20, 2018. 14 pages.

Wen et al., A weighted ML-KNN based on discernibility of attributes to heterogeneous sample pairs, Information Processing and Management (2022) 59:103053, 21 pages.

Wilkinson et al., Electrocutaneous pain thresholds are higher during systole than diastole, Biological Psychology (2013) 94:71-73, 3 pages.

Xu et al., Anxious brain networks: A coordinate-based activation likelihood estimation meta-analysis of resting-state functional connectivity studies in anxiety, Neuroscience and Biobehavioral Reviews (2019) 96:21-30, 10 pages.

Yearsley et al., Quantum cognition and decision theories: A tutorial, Journal of Mathematical Psychology (2016) 74:99-116, 18 pages.

Yildirim et al., A modified feature selection method based on metaheuristic algorithms for speech emotion recognition, Applied Acoustics vol. 173, Feb. 2021,107721, 11 pages.

Yu et al., Deep attention based music genre classification, Neurocomputing (2020) 372:84-91, 8 pages.

Zernadji et al., Integrating quality requirements in engineering web service orchestrations, The Journal of Systems and Software (2016) 122:463-483, 21 pages.

Zhou et al., Controllable storage and retrieval of optical solitons in triple quantum dot molecules by inter-dot tunneling coupling effect, Physics Letters A (2022) 448:128320, 6 pages.

\* cited by examiner

US 11,694,786 B1

RECOMMENDATION METHODS, SYSTEMS AND DEVICES

RELATED APPLICATIONS

The subject application claims benefit of and priority to U.S. provisional patent application Nos. 62/788,656, filed 4 Jan. 2019, and 62/788,908, filed 6 Jan. 2019, each disclosure of which is herein incorporated by reference in its entirety.

FIELD OF THE DISCLOSURE

Some embodiments of the present disclosure relate to systems, devices, and methods for making recommendations to users for, individually or together, goods, services, and information/media (e.g., audio, video, publications), as well as veracity of data/information, based upon an emotional impact of such goods/services and/or media/information on the user, other users, and/or other individuals, as well some embodiments directed to systems, devices, and methods for treating one or more brain functions, including neurological conditions and episodes associated therewith by determining (and optionally providing) media (e.g., audio, but in some embodiments, any of audio, textual information, and video), which may be referred to as optimal medical media ("OMM").

BACKGROUND

The efficacy of recommendation systems and methods, and the field of psychographics, have evolved to improve our ability to match the right product/service/item with the right customer/user. While this practice has extended into media, systems employing such functionality leave much to be desired, as such systems function so as to selecting media of a certain genre that either the listener/viewer/user has preselected, or, the system monitors the listener/viewer/user's past selections, and presents similar selections to respective listeners/viewers/users. Moreover, present recommendation systems/methods for product/service need improvement.

SUMMARY OF AT LEAST SOME OF THE EMBODIMENTS

Group I

Group I embodiments are directed to systems, devices, and methods for making recommendations to users for, individually or together, goods, services, and information/media (e.g., audio, video, publications) based upon an emotional impact of such goods/services and/or media on the user, other users, and/or other individuals, as well as embodiments directed to methods, systems and devices for determining the veracity of media information (e.g., news) based upon emotional impact of such media upon one or more other users and/or individuals (similarly, "other users" and "other individuals" may be persons having similar personality type, background, gender, age, geographic location, and the like, for (example).

Accordingly, some Group I embodiments of the present disclosure are directed to systems, devices, and methods for market analytics and/or user recommendation of digital information (for example). Accordingly, in some embodiments, such a market analytics/user recommendation methods comprise identifying one or more correlations between at least one of one or more sentient agents and one or more non-sentient agents associated with corresponding systems, determining at least one psychometric profile for each, the psychometric profile comprising an Emotional Impact Factor (EIF), and determining at least one market, and/or at least one recommendation for at least one of information, product, and service, using each EIF, for at least one user. Such embodiments may further include providing the at least one market and/or recommendation to at least one user.

Such embodiments (as well as others) may include one and/or another, and in some embodiments a plurality, and in some embodiments, all of the following additional features, functions, steps, structure, and clarifications, leading to yet further embodiments:

- determining the EIF may comprise connecting a plurality of data points,
  - the connecting may be configured for identifying at least one parameter;
    - the at least one parameter including anthropological, ethnographic, and psycho-social factors;
- determining the EIF may include integrating and/or weighting of the one or more parameters, and/or integrating and/or weighting of the one or more additional factors;
- determining the EIF may comprise or may further comprise at least one of: text-based analysis of annotations of songs, indexing, media analysis, and principle component analysis;
- determining the EIF may comprise or may further comprise examining structured or unstructured behavior data of at least one user;
  - such structured or unstructured data may be from one or more defined networks and/or systems, where the defined networks and/or systems may comprise at least one of: streaming services, platforms, and peer-to-peer networks;
- a respective EIF may be determined through an analysis of a limited number of parameter, for example, n>12 parameters;
- the EIF may be configured for use with a media recommendation system, where, for example, the media recommendation system may comprise a sales recommendation system configured to match at least one product with the at least one user;
- the one or more parameters may comprise at least one of: previous consumption within a given recommendation system, one or more platforms, and one or more peer-to-peer network transactions over a predetermined period of time;
- weighting of the one or more parameters may comprise increasing weighting of the transactions over the predetermined period of time;
- the EIF may be configured for use for at least one of analyzing, visualizing, and recommending media content for at least one user; and
- the one or more sentient agents may be configured to determine a relationship between at least one of a user's: emotional quotient, psychometric profile, and the EIF of content available for consumption on a given media service, platform, and/or peer-to-peer network.

In some embodiments, a market analytics/user recommendation system is provided. Such a system, according to some embodiments, includes at least one processor having code operating thereon configured to cause the at least one processor to identify one or more correlations between at least one of one or more sentient agents and one or more non-sentient agents associated with corresponding systems, determine at least one psychometric profile for each, the psychometric profile comprising an Emotional Impact Factor (EIF), and determining at least one market, and/or at least one recommendation for at least one of information, product, and service, using each EIF for at least one user.

Such embodiments (as well as others) may include one and/or another, and in some embodiments a plurality, and in some embodiments, all of the following additional features, functions, steps, structure, and/or clarifications, leading to yet further embodiments:

the code may be further configured to cause the at least one processor to provide the at least one market and/or recommendation to at least one user;

the code for causing the at least one processor to determine the EIF may comprise code for causing the at least one processor to connect a plurality of data points, where connecting may be configured for identifying at least one of anthropological, ethnographic, and psychosocial factors;

the code for causing the at least one processor to determine the EIF may include code to cause the at least one processor to integrate and/or weight the one or more parameters, and/or integrate and/or weight the one or more additional factors;

the code for causing the at least one processor to determine the EIF comprises or further comprises code for causing the at least one processor to textually analyze annotations of songs, indexing, media analysis, and principle component analysis;

the code for causing the at least one processor to determine the EIF may comprise or may further comprise code for causing the at least one processor to examine structured or unstructured behavior data of at least one user;

where the structured or unstructured data may be from one or more defined networks and/or systems;

the defined networks and/or systems may comprise at least one of: streaming services, platforms, and peer-to-peer networks;

the code for causing the at least one processor to determine the EIF may include code for causing the at least one processor to determine a respective EIF via an analysis of a plurality or parameters, and in some embodiments, such "n" parameters may be greater than 12;

a media recommendation system;

the media recommendation system may comprise a sales recommendation system configured to match at least one product with at least one user;

the one or more parameters may comprise at least one of: previous consumption within a given recommendation system, one or more platforms, and one or more peer-to-peer network transactions over a predetermined period of time;

weighting of the one or more parameters may comprise increasing weighting of the transactions over the predetermined period of time;

the EIF may be configured for use for at least one of analyzing, visualizing, and recommending media content for at least one user;

the one or more sentient agents may be configured to determine a relationship between at least one of a user's: emotional quotient, psychometric profile, and the EIF of content available for consumption on a given media service, platform, and/or peer-to-peer network;

the at least one processor may comprise at least one networked server;

the at least one processor may comprise at least one client computer; and the system may further comprise at least one mobile device in wired or wireless communication with the at least one processor;

where the at least one mobile device may comprise a plurality of mobile devices each associated with a particular user (for example).

Some embodiments of the present disclosure are directed to systems, devices, and methods for a false-media identification method. Such embodiments comprise reviewing one or more pieces of media, where each piece of media includes a source, determining at least one emotional impact factor (EIF) for each piece of media, and associating each EIF is a number or alphanumeric. The number or alphanumeric corresponds to a falseness scale, such that, in some embodiments, upon the associated EIF being greater than a predetermined threshold on the scale, the media may be flagged as false (or true, or presented to one or more users/viewers as a scale of veracity or falseness).

In some such embodiments:

determining the EIF may be configured for a specific audience, where the audience may be one based on, for example, at least one of socio-economic status and educational level; and/or the method may further include notifying consumers of the one or more pieces of media of flagged false media Such method embodiments may be embodied in a device and/or system comprising at least one processor having code operating thereon configured to cause the at least one processor to perform the methodology above, as well as a mobile application configured for operation on, used or in combination with a mobile application and/or device. Moreover, such a mobile application may be configured to at least one of send, receive, and/or process information from the at least one processor according to the disclosed system embodiments. See General Embodiments below.

In some embodiments, data collected (and thus stored), and any other data associated with one or more users, individuals, and agents, and the like, can be used by an artificial intelligence (AI) component of the systems and methods disclosed. For example, such data can be used to train the AI to identify and/or interact with the sentient and/or non-sentient agents, and/or trained to determine either EIFs and/or recommendations. In some embodiments, the AI component may include interaction with an AI bot (AIB) by users and/or agents.

Group II

Group II embodiments are directed to systems, devices, and methods for treating one or more brain functions, including neurological conditions and episodes associated therewith.

Accordingly, in some such embodiments, a brain function medical treatment method comprising at least one of receiving first data corresponding to input from at least one patient (user) with respect to answers to a series questions (Q&A) during a period at which the at least one user is not experiencing an episode or a condition associated with at least one brain function, and selecting, by the at least one user, at least one medical media parameter. As a result of at least one of the first data, user selection, and interactive artificial intelligence (AI), where the AI optionally comprises or includes interaction with an AI bot (AIB), identifying OMM configured to counteract the at least one user experiencing the episode or the condition from entering at least one of a fugue state and a dissociative state. The method may also include, in some embodiments, repeating the previous steps.

Such embodiments, as well as others, may further comprise one and/or another (and in some embodiments, a plurality of, and in some embodiments, all of) of the following features, clarifications, functionality, steps, and structure, yielding yet further embodiments:
- the OMM may be configured as a treatment or well-being plan for treating the episode or condition;
- the OMM may be configured as at least one of one or more musical pieces, videos, and readings;
  - the at least one of the one or more musical pieces, videos, and readings may be configured as at least one playlist;
  - the at least one playlist is configured to treat a specific episode or condition;
  - the condition is selected from the group consisting of: distress, flow-state, weight-loss, and concentration;
- playing the OMM for/by the user for treatment of the at least one episode or condition;
- the OMM may be configured with a guiding component;
- determining the efficacy of the OMM with respect to the at least one episode or condition;
- providing feedback information on use of the OMM for treatment of the at least one episode or condition by at least one of the user, a medical professional, and the AIB;
- tracking secondary information;
  - the secondary information may comprise at least one of health data, and personal data;
  - health data may comprise at least one of heartrate, blood pressure, and temperature;
  - the personal data may comprise at least one of caloric intake, exercise data, sleep data, and fluid intake data; and
  - feedback information may include alerts to users, suggestions of different media and combinations thereof, recommendations to connect with their physicians, historical user consumption, and the like;
- producing a report, where the report may include data collected, analyzed and/or determined;
- collecting medication data of the at least one user, where the medication information can comprise information related to pharmaceutical use;
- training the AI using at least one of user selection of parameters, feedback information, the secondary information, and medication information;
- identifying an emergency or potential emergency;
  - such emergencies may be identified by aberrations in user-behavior;
- recognizing patterns for the at least one user so as to identify trends in the at least one user with respect to selection of specific words indicative of a neurological condition;
  - the condition can be any of (for example) anxiety disorders, mood disorders, personality disorders, stress, and general health or wellness;
- the episode is a measurable or self-identified psychophysical disease or discomfort;
- notifying at least one of the user and one or more individuals associated with the at least one user, regarding, the identification of any of a condition, episode, and behavior;
  - notifying comprises at least one of email, text, phone, and/or any method of secure direct in-application communication;
- secondary information, which may comprise at least one of: heart information, activity information, meal information, fluid-intake information;
- determining, based on at least the secondary information, whether the at least one user is within or outside of a state;
- the state may comprise, for example, a flow state or an emergency state;
- providing or associated an account for each of the at least one users;
  - for such accounts, collecting or aggregating funds for each account from a third party;
  - the third party may comprise an insurance provider;
  - the funds may comprise at least one incentive, where the incentive may comprise goods, services, and/or monetary compensation;
- selling data collected, analyzed, and/or otherwise produced by the method;
- using the OMM so as to train the at least one user to develop new habits through behavior modification;
  - training, for the at least one user, may comprise at least one of centering, practicing neuro-feedback, and mindfulness, then returning to a state of productivity;
- delay a length of time treatment of the at least one of the neurological episode and condition;
- configured the method to, in the at least one user, at least one of allay a fugue state, a panic attack, and achieve a dopaminergic state;
- a playlist may comprise a plurality of playlists each corresponding to a type including one or more of the following characteristics: variation of time signature, absence of minor keys, instrumentation, e.g., organic instrumentation (that is, non-modified via electronics, for example, acoustic instrumentation), variation of instrumentation, absence of dissonance, balanced audio recording, limitation of decibel level, pre-set decibel level, familiarity, length of play, continuous play, intermission length, dopaminergic effect, and anxiolytic effect;
- manipulation of the OMM by at least one of the at least one user and a medical professional;
- using the AI in creating at least one modifiable STEM for at least one media of the OMM;
  - the modifiable STEM may be modifiable by the at least one user;
  - the STEM may be modifiable via the key;
- the OMM comprises at least one song and includes a video component comprising lyrics corresponding to the at least one song configured such that the at least one user can sing the song;
- the OMM may be derived or otherwise based on recorded compositions from Baroque, classical, and neoclassical periods;
  - the compositions may be augmented;
- the AI at least partially configures the OMM;
- the configuring the medical media comprises remixing STEMs associated with the OMM;
- the OMM comprises at least one STEM, and wherein the STEM corresponds to a core element; and
- the AI, after user selection of at least one parameter, composes and one or more pieces of the OMM;
  - composing the one or more pieces of the OMM may comprise remixing one or more STEMs associated with the OMM;
  - the at least one STEM may comprise a plurality of STEMs;
  - each STEM may correspond to a respective core element; and
  - the plurality of STEMs, and thus, core elements, configured to interact with one another to produce a desired affect, where, in some embodiments, the OMM is configured to produce the desired effect.

In some embodiments, a brain function medical treatment system is provided and comprises at least one processor having code operating thereon configured to cause the at least processor to receive first data corresponding to input from at least one patient (user) with respect to answers to a series questions (Q&A) regarding a period at which the at least one user is not experiencing an episode or a condition associated with at least one brain function, select, by the at least one user, at least one medical media parameter, operate as or access an interactive artificial intelligence (AI), wherein the AI optionally includes or is configured as an AI bot (AIB), and is configured to identify OMM configured to counteract the episode or the condition the at least one user experiences from entering at least one of a fugue state and a dissociative state, and optionally repeating one or more of receiving, selecting, and operating.

Such embodiments, as well as others, may further comprise one and/or another (and in some embodiments, a plurality of, and in some embodiments, all of) of the following features, clarifications, functionality, steps, and structure, yielding yet further embodiments:

the code may be further configured to cause the at least one processor to perform or otherwise conform with the one and/or another of the steps, functionality, or clarifications recited above with reference to the embodiments included in paragraph [0004];

the code may be further configured to cause the at least one processor to perform or otherwise conform; and the at least one of the at least one processor may comprise a server;

Systems according to some of the above-noted embodiments, may also, for example, include a mobile application configured for operation on, used or in combination with a mobile device. Moreover, such a mobile application may be configured to at least one of send, receive, and/or process information from the at least one processor. See General Embodiments below.

Group II Embodiments

Group III embodiments comprise any combination of systems, methods, and devices with respect to the above-noted embodiments (as well as any other embodiments disclosed herein), including, any combination of components, steps, structure, and functionality thereof.

Any of the above noted embodiments can be embodied in computer code operational on a computer (server, client, mobile, and the like) or computer system or platform, which causes the computer/platform to perform any and all of the noted methods disclosed, as well as non-transitory computer readable media. See, e.g., General Embodiments, below.

These and other embodiments, objects, and advantages of the various group of embodiments will become even more evident with reference to the associated drawings filed herewith and briefly described below, as well as the following detailed description for at least some of the embodiments.

DETAILED DESCRIPTION FOR AT LEAST SOME EMBODIMENTS

General Embodiments

Figure 1:
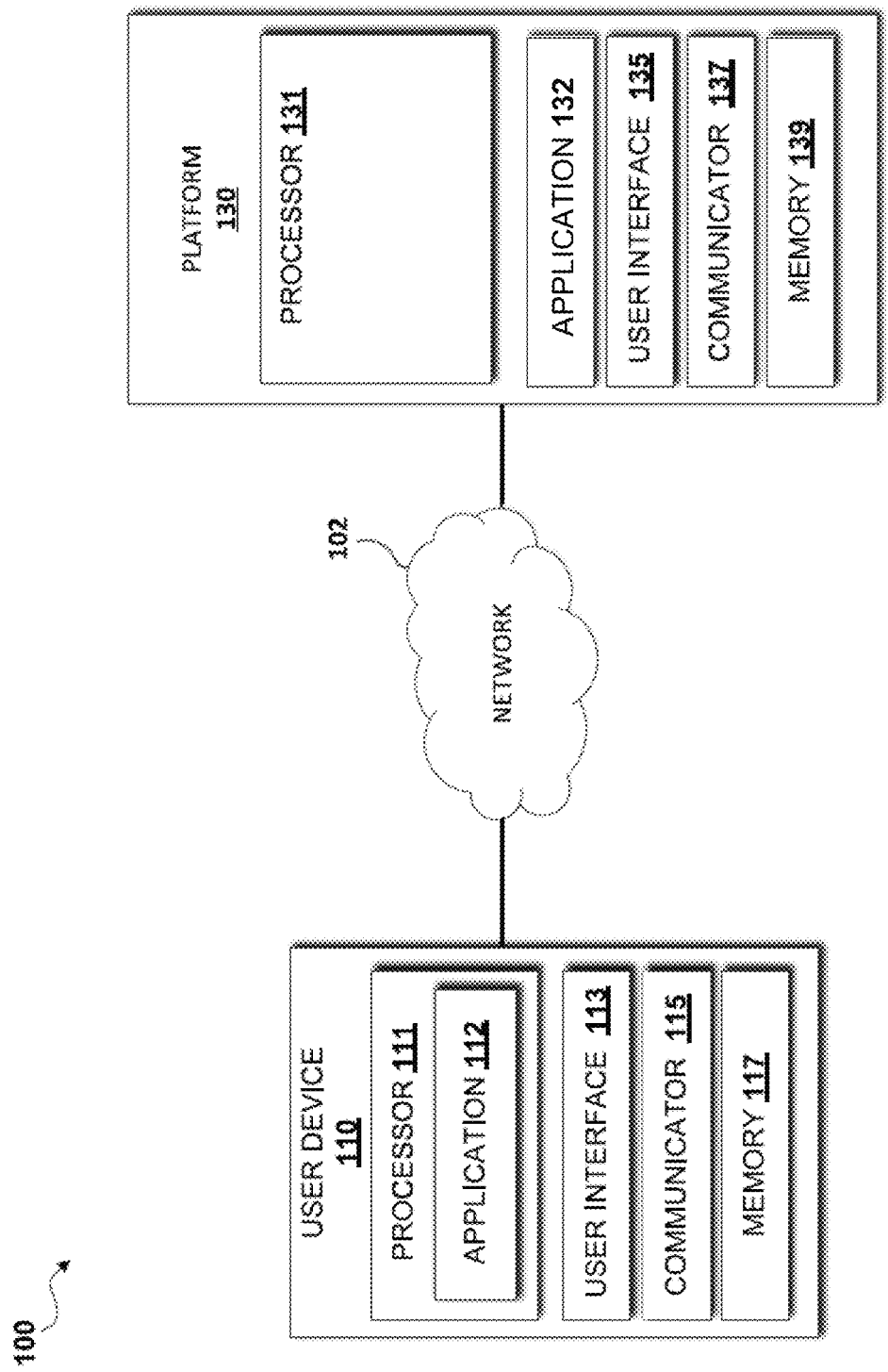
FIG. 1 is a functional block diagram depicting a general system (which in some embodiments, can be considered a device, and/or components of a system/device), according to some embodiments of the present disclosure.

FIG. 1 is a schematic block diagram depicting general device and system embodiments, configured to at least enable operation of the devices, systems and methods (and methods of Groups I-III operational thereon) according to at least some of the embodiments of Group I-III disclosed herein (see above, and below). To this end, as shown, system 100 can include user device 110 and platform 130 (e.g., recommendations platform), interconnected over network 102. While system 100 is shown as including two discrete devices, other arrangements can be contemplated (e.g., two or more discrete elements). Moreover, one and/or another of the functionalities of the various components of the user device and platform can be combined into a single device/system.

Network 102 can be or include, for example, an intranet, a local area network (LAN), a personal area network (PAN), a wireless local area network (WLAN), a wireless personal area network (WPAN), a wide area network (WAN) such as the Internet, a metropolitan area network (MAN), a worldwide interoperability for microwave access network (WiMAX®), an optical fiber (or fiber optic)-based network, a Wi-Fi™ network, a Bluetooth® network, a virtual network, and/or any combination thereof. Network 102 can include, for example, wired connections, wireless (e.g., radio communication, free-space optical communication) connections, fiber optic connections, and the like. Network 102 can include, for example, routers, firewalls, switches, gateway computers, edge servers, and the like. In some instances, network 102 can alternatively or otherwise include, for example, telecommunications, data communications, and/or data transmission channel, link, connection, or path, by which data and signals can be communicated, transmitted, or propagated between and amongst devices. For example, network 102 can include a near-field communications (NFC) connection (e.g., NFC beacon connection), a short-range or short-link communications connection (e.g., Bluetooth®), and/or the like. Network 102 can include any suitable combination of connections and protocols configured to enable and support interconnection, communications, and interoperations between user device 110 and platform 130.

User device 110 and platform 130 can individually and respectively include, for example, a device, node, system, or platform, such as a machine or compute device, compute system, compute platform, information system, programmable electronic device, information content processing device, and/or the like. For example, user device 110 and/or platform 130 can include, for example, a controller, a processor, a mobile phone, a smart phone, a tablet computer, a laptop computer, a personal or desktop computer, a server (e.g., database server), a virtual machine, a wearable device (e.g., electronic watch), an implantable device, and/or the like. User device 110 and/or platform 130 can otherwise be, include, or use any suitable type and combination of devices, systems, and/or platforms, capable of communicating or interoperating (e.g., via network 102) with one or more other devices, systems, and/or platforms, such as user device 110 and/or platform 130. In some embodiments, user device 110 and/or platform 130 may include internal and external hardware components, such as described with reference to FIG. 2. In other embodiments, user device 110 and/or platform 130 may be implemented in a cloud-computing environment, such as described with reference to FIGS. 3-4.

User device 110 includes processor 111, user interface 113, communicator 115, and memory 117. User device 110 can be configured to implement any suitable combination of devices and technologies, such as network devices and device drivers, to support the operation of processor 111, user interface 113, communicator 115, and memory 117, and provide a platform enabling communications (e.g., via network 102) between user device 110 and platform 130.

Processor 111 can be or include any suitable type of processing device configured to run and/or execute software, code, commands, or logic. For example, processor 111 can be or include a hardware-based integrated circuit (IC), a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), or the like. Processor 111 can be operatively coupled to memory 117, such as by way of a data transfer device or system such as a bus (e.g., address bus, data bus, control bus). Processor 111 can otherwise include a processor configured to execute any suitable type or form of software, code, commands, and/or logic, corresponding to or representative of an application or program such as application 112, as described herein.

Application 112 (e.g., methodology of the embodiments of any of Groups I-III) can be or include any suitable type of application or program, such as a software or computer program, one or more subroutines contained in a program, an application programming interface, or the like. Application 112 can include any suitable type or form of software, code, commands, and/or logic representing instructions, such as machine-, computer-, or processor-executable code, logic, instructions, commands, and/or the like. Application 112 can be configured to reside or be hosted at user device 110. For example, application 112 can be configured be stored (e.g., via memory 117) at user device 110. Alternatively or in combination, application 112 can be configured to reside or be hosted at a device separate, distinct, or remote from user device 110, such as at a server, node, and/or the like. Application 112 can be configured to be run or executed by, at, or via any suitable type of processor or processing device, such as processor 111. For example, application 112 can be or include a native application, a web or web-based application, and/or a hybrid application (e.g., an application having a combination of native and web-based application characteristics or functionality).

User interface 113 can be or include any suitable type of user interface device configured to enable user interaction between a user and user device 110. In some embodiments, user interface 113 can be configured to enable user interaction between user (e.g., at user device 110) and platform 130, as described herein. For example, user interface 113 can be configured to provide (e.g., display) output (e.g., from application 132). Further, user interface 113 can be configured to receive user input (e.g., from a user at user device 110), as described herein. For example, user interface 113 can include one or more input devices such as a keyboard and mouse, and one or more output devices such as displays, screens, projectors, and the like. As another example, user interface 113 can include one or more input/output (I/O) devices, such as a touchscreen, a holographic display, a wearable device such as a contact lens display, an optical head-mounted display, a virtual reality display, an augmented reality display, and/or the like. User interface 113 can be configured to implement any suitable type of human-machine interface device, human-computer interface device, a batch interface, graphical user interface (GUI), and the like. User interface 113 can otherwise include or be configured to implement any suitable type of interface (e.g., user interface 113) capable of embodiment in conjunction with a device such as platform 130, such as to provide for user interaction between a user and the device, as described herein. In some embodiments, the user input received at user interface 113 can be sent (e.g., over network 102) to platform 130 for execution thereat.

Communicator 115 can be or include, for example, a hardware device operatively coupled to processor 111 and memory 117, and/or software stored in memory 117 and executable by processor 111, capable of enabling and supporting communications over a network (e.g., network 102) and/or directly between or among compute devices (e.g., user device 110 and platform 130), as well as devices for local alert (e.g., audible or visual signaling, via a speaker/headphone and screen or indicator light, respectively). For example, communicator 115 can be or include a network interface card (NIC), a network adapter such as a Transmission Control Protocol (TCP)/Internet Protocol (IP) adapter card or wireless communication adapter (e.g., a 4G wireless communication adapter using Orthogonal Frequency Division Multiple Access (OFDMA) technology), a Wi-Fi™ device or module, a Bluetooth® device or module, and/or any other suitable wired and/or wireless communication device. Communicator 115 can be configured to connect or interconnect user device 110 and one or more other devices (e.g., platform 130) for data communications therebetween, such as over a communications network (e.g., network 102). Communicator 115 can be configured to be implemented in conjunction with any suitable architecture, such as one designed for passing data and/or control information between processors (e.g., processor 111, processor 131), system memory (e.g., memory 117, memory 139), peripheral devices (e.g., user interface 113, user interface 135), and any other devices or components (e.g., of system 100 and/or including platform 130).

Memory 117 can be or include any suitable type of memory, data storage, or machine-, computer-, or processor-readable media capable of storing a machine or computer program, digital information, electronic information, and the like (e.g., of or associated with application 112). For example, memory 117 can be configured to store an application or program such as application 112, such as for execution by processor 111. Memory 117 can be or include a memory buffer, a hard drive, a magnetic disk storage device of an internal hard drive, magnetic tape, magnetic disk, optical disk, portable memory (e.g., flash drive, flash memory, portable hard disk, memory stick), a semiconductor storage device such as a random access memory (RAM) (e.g., RAM including cache memory), a read-only memory (ROM), an erasable programmable read-only memory (EPROM), an electrically erasable programmable read-only memory (EEPROM), and/or the like. Memory 117 can otherwise include any suitable type of memory or data storage, as such may be chosen as a matter of design.

Platform 130 includes, for example, processor 131, application 132 (which may be included as code residing on processor 131, and may be an application to perform, e.g., methodology of the embodiments of any of Groups I-III), user interface 135, communicator 137, and memory 139. Platform 130 can be configured to implement any suitable combination of devices and technologies, such as network devices and device drivers, to support the operation of processor 131, application 132, user interface 135, communicator 137, and memory 139, and provide a platform enabling communications (e.g., via network 102) between user device 110 and platform 130, as described herein. Platform 130 can be configured to make recommendations (e.g., via application 132). While platform 130 is shown as including certain discrete elements or components (e.g., processor 131, application 132, user interface 135, communicator 137, memory 139), other arrangements can be contemplated. For example, in some embodiments, platform 130 can alternatively or otherwise include processor 131, application 132, user interface 135, and memory 139, and/or any other number of discrete elements or components (e.g., including one or more integrated or separate devices, platforms, nodes, etc.), as such may be chosen as a matter of design. In some embodiments, the platform 130 can comprise a device, system, or platform such as a recommendations system according to the disclosed embodiments, Processor 131 can be or include any suitable type of processing device configured to run and/or execute software, code, commands, or logic. For example, processor 131 can be or include a hardware-based integrated circuit (IC), a general purpose processor, a central processing unit (CPU), an accelerated processing unit (APU), an application specific integrated circuit (ASIC), a field programmable gate array (FPGA), a programmable logic array (PLA), a complex programmable logic device (CPLD), a programmable logic controller (PLC), or the like. Processor 131 can be operatively coupled to memory 139, such as by way of a data transfer device or system such as a bus (e.g., address bus, data bus, control bus). Processor 131 can otherwise include a processor configured to execute any suitable type or form of software, code, commands, and/or logic, corresponding to or representative of an application or program such as application 132, as described herein.

Figure 2:
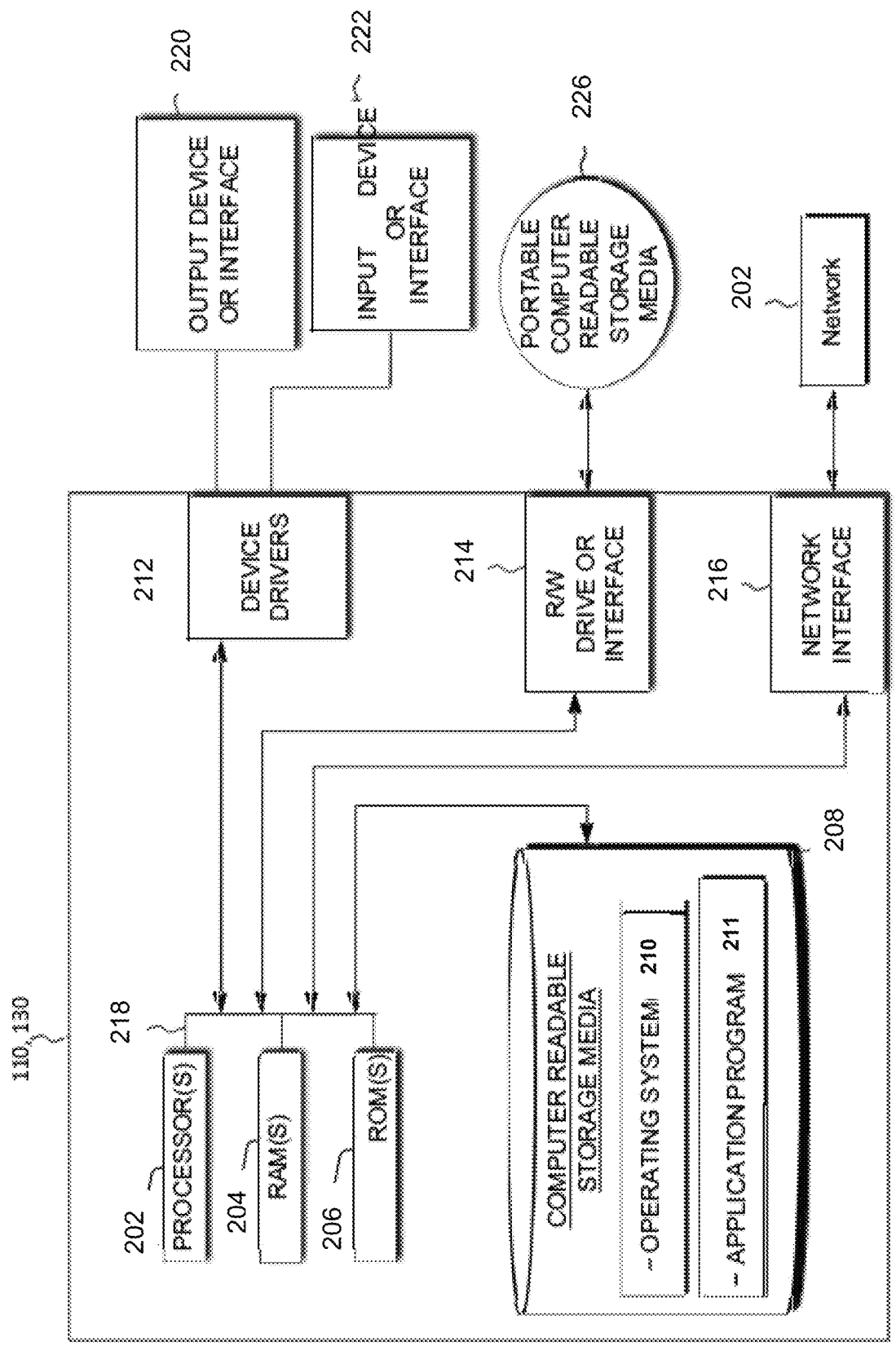
FIG. 2 is a block diagram depicting a user device and system, according to some embodiments, for performing/ accomplishing methodology according to any of the embodiments of Groups I-III.

FIG. 2 is a block diagram depicting user device 110 and/or system 130, in accordance with some embodiments of the present disclosure. As shown, user device 110 and/or system 130 may include one or more processors 202 (e.g., microprocessors, CPUs, GPUs, etc.), one or more computer-readable RAMs 204, one or more computer-readable ROMs 206, one or more computer readable storage media 208, device drivers 212, read/write drive or interface 214, network adapter or interface 216, all interconnected over a communications fabric 218. The network adapter 216 communicates with a network 230. Communications fabric 218 may be implemented with any architecture designed for passing data and/or control information between processors (such as microprocessors, communications and network processors, etc.), system memory, peripheral devices, and any other hardware components within a system.

One or more operating systems 210 and one or more application programs 211 (e.g., those for performing at least some, and in some embodiments, all of the methodology of the embodiments of Groups I-III), such as secure application 132, residing on platform 130, are stored on one or more of the computer readable storage media 208 for execution by one or more of the processors 202 via one or more of the respective RAMs 204 (which typically include cache memory). In some embodiments, each of the computer readable storage media 208 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable medium (e.g., a tangible storage device) that can store a computer program and digital information.

User device 110 and/or system 130 may also include a read/write (R/W) drive or interface 214 to read from and write to one or more portable computer readable storage media 226. Application programs 211 on viewing device 110 and/or user device 120 may be stored on one or more of the portable computer readable storage media 226, read via the respective R/W drive or interface 214 and loaded into the respective computer readable storage media 208. User device 110 and/or system 130 may also include a network adapter or interface 216, such as a Transmission Control Protocol (TCP)/Internet Protocol (IP) adapter card or wireless communication adapter (such as a 4G wireless communication adapter using Orthogonal Frequency Division Multiple Access (OFDMA) technology). For example, application programs 211 may be downloaded to the computing device from an external computer or external storage device via a network (for example, the Internet, a local area network or other wide area network or wireless network) and network adapter or interface 216. From the network adapter or interface 216, the programs may be loaded onto computer readable storage media 208. The network may include copper wires, optical fibers, wireless transmission, routers, firewalls, switches, gateway computers and/or edge servers. User device 110 and/or system 130 may also include one or more output devices or interfaces 220 (e.g., a display screen), and one or more input devices or interfaces 222 (e.g., keyboard, keypad, mouse or pointing device, touchpad). For example, device drivers 212 may interface to output devices or interfaces 220 for imaging, to input devices or interfaces 222 for user input or user selection (e.g., via pressure or capacitive sensing), and so on. The device drivers 212, R/W drive or interface 214 and network adapter or interface 216 may include hardware and software (stored on computer readable storage media 208 and/or ROM 206).

System 130 can be a standalone network server or represent functionality integrated into one or more network systems. User device 110 and/or system 130 can be a laptop computer, desktop computer, specialized computer server, or any other computer system known in the art. In some embodiments, system 130 represents computer systems using clustered computers and components to act as a single pool of seamless resources when accessed through a network, such as a LAN, WAN, or a combination of the two. This embodiment may be desired, particularly for data centers and for cloud computing applications. In general, user device 110 and/or system 130 can be any programmable electronic device or can be any combination of such devices, in accordance with embodiments of the present disclosure.

The programs described herein are identified based upon the application for which they are implemented in a specific embodiment or embodiment of the present disclosure. That said, any particular program nomenclature herein is used merely for convenience, and thus the embodiments and embodiments of the present disclosure should not be limited to use solely in any specific application identified and/or implied by such nomenclature.

Embodiments of the present disclosure (e.g., especially those of Groups I-III) may be or use one or more of a device, system, method, and/or computer readable medium at any possible technical detail level of integration. The computer readable medium may include a computer readable storage medium (or media) having computer readable program instructions thereon for causing a processor to carry out one or more aspects of the present disclosure.

The computer readable (storage) medium can be a tangible device that can retain and store instructions for use by an instruction execution device. The computer readable medium may be, but is not limited to, for example, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire, in accordance with embodiments of the present disclosure.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform various aspects of the present disclosure. Aspects of the present disclosure are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine or system, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks, in accordance with embodiments of the present disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Flowchart and block diagrams as shown in the drawings (see, e.g., FIGS. 5 and 6) illustrate at least some of the architecture, functionality, and operation of some embodiments of systems, methods, and computer readable media according to various embodiments of the present disclosure. In this regard, each block in the flowchart or block diagrams may represent a module, segment, or portion of instructions, which includes one or more executable instructions for implementing the specified logical function(s). In some embodiments, the functions noted in the blocks may occur out of the order noted in the Drawings. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be understood that although this disclosure includes a detailed description on cloud computing, embodiment of the teachings recited herein are not limited to a cloud-computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics can include: on-demand self-service: a cloud consumer can unilaterally provision computing capabilities, such as server time and network storage, as needed automatically without requiring human interaction with the service's provider; broad network access: capabilities are available over a network and accessed through standard mechanisms that promote use by heterogeneous thin or thick client platforms (e.g., mobile phones, laptops, and PDAs); resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter); rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time; measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows: software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings. Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations. Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows: private cloud: the cloud infrastructure is operated solely for an organization. It may be managed by the organization or a third party and may exist on-premises or off-premises. Community cloud: the cloud infrastructure is shared by several organizations and supports a specific community that has shared concerns (e.g., mission, security requirements, policy, and compliance considerations). It may be managed by the organizations or a third party and may exist on-premises or off-premises. Public cloud: the cloud infrastructure is made available to the general public or a large industry group and is owned by an organization selling cloud services. Hybrid cloud: the cloud infrastructure is a composition of two or more clouds (private, community, or public) that remain unique entities but are bound together by standardized or proprietary technology that enables data and application portability (e.g., cloud bursting for load-balancing between clouds). A cloud-computing environment is service oriented with a focus on statelessness, low coupling, modularity, and semantic interoperability. At the heart of cloud computing is an infrastructure that includes a network of interconnected nodes.

Figure 3:
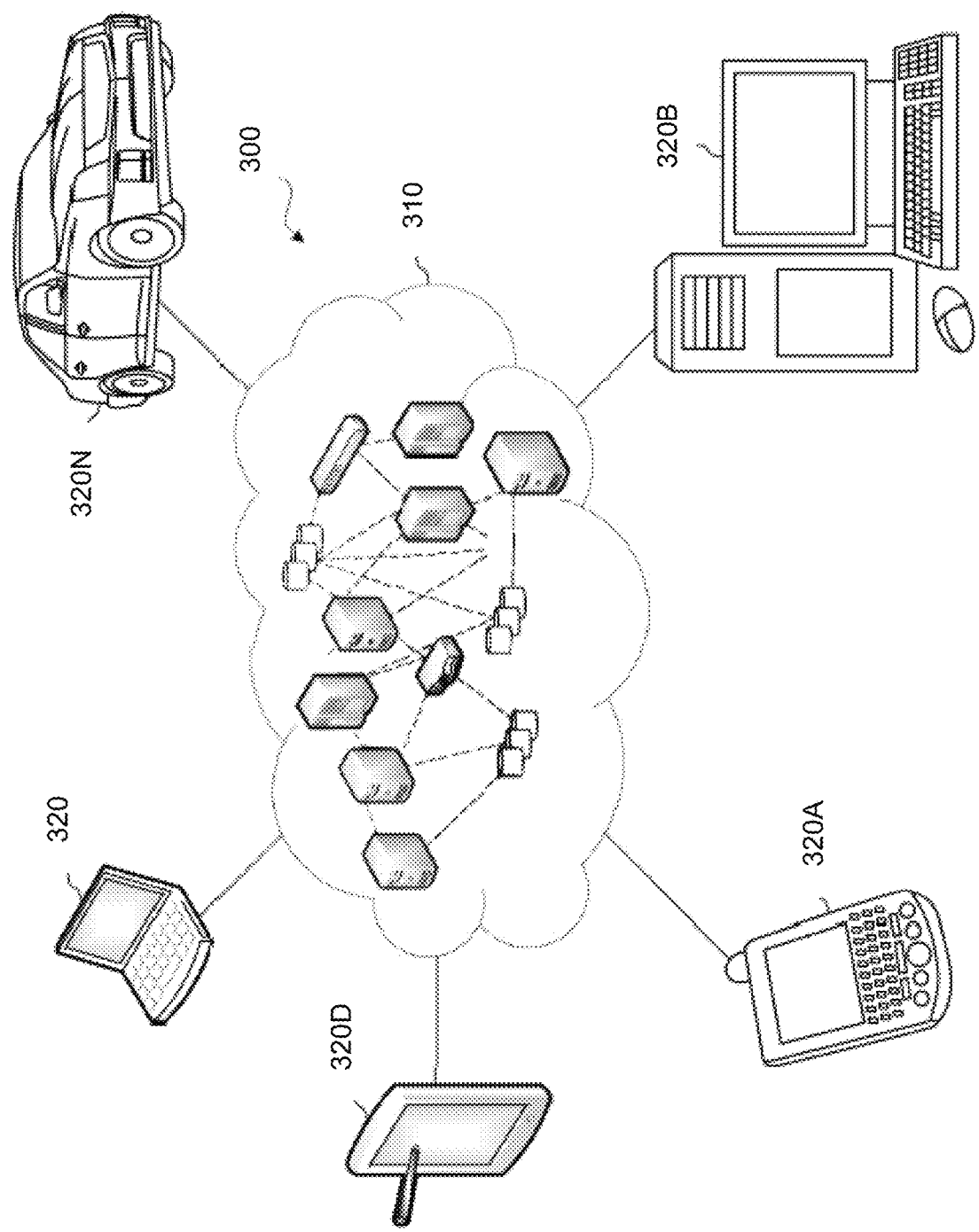
FIG. 3 depicts a cloud computing environment of the device/system for Groups I-III.

Referring now to FIG. 3, illustrative cloud computing environment 300 is depicted. As shown, cloud computing environment 300 includes one or more cloud computing nodes (not depicted) with which local computing devices used by cloud consumers, such as, for example, personal digital assistant (PDA) or cellular telephone 320A, desktop computer 320B, laptop computer 320C, and/or automobile computer system 320n may communicate. The one or more cloud computing nodes may communicate with one another. They may be grouped (not shown) physically or virtually, in one or more networks, such as Private, Community, Public, or Hybrid clouds as described hereinabove, or a combination thereof. This allows cloud-computing environment 300 may be implemented to offer infrastructure, platforms, and/or software as services for which a cloud consumer does not need to maintain resources on a local computing device. The types of computing devices 320A-N, as shown in FIG. 4, are intended to be illustrative only and that the one or more computing nodes and cloud computing environment 300 can communicate with any type of computerized device over any type of network and/or network addressable connection (e.g., using a web browser).

Figure 4:
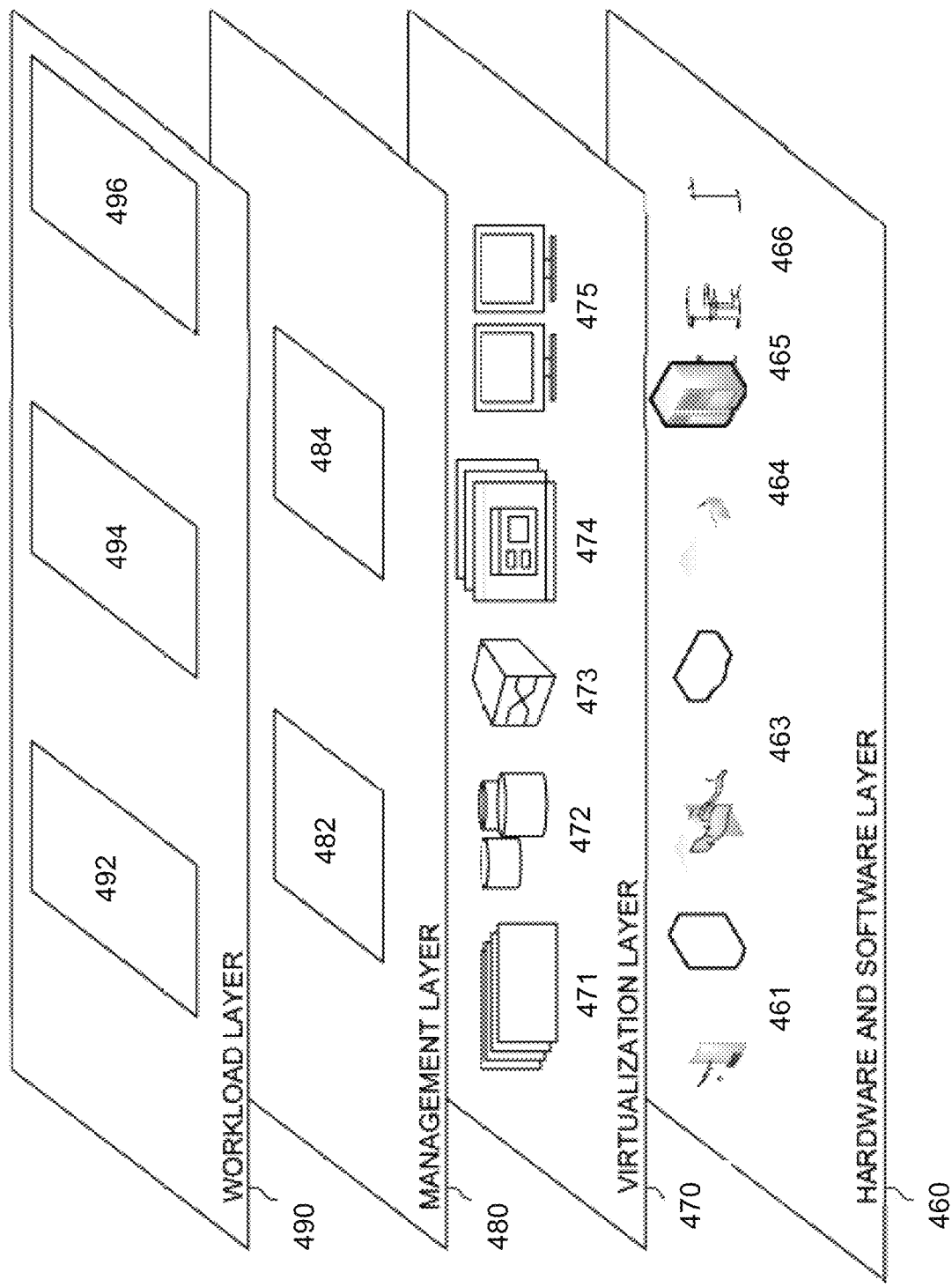
FIG. 4 depicts abstraction model layers of the device/system for the embodiments of Groups I-III.

Referring now to FIG. 4, a set of functional abstraction layers provided by cloud computing environment 300 is shown. The components, layers, and functions are intended to be illustrative only, and embodiments of the present disclosure are not limited thereto. As depicted, the following layers and corresponding functions are provided.

Hardware and software layer 460 includes hardware and software components. Examples of hardware components include: mainframes 461; RISC (Reduced Instruction Set Computer) architecture based servers 462; servers 463; blade servers 464; storage devices 465; and networks and networking components 466. In some embodiments, software components include network application server software 467 and database software 468. Virtualization layer 470 provides an abstraction layer from which the following examples of virtual entities may be provided: virtual servers 471; virtual storage 472; virtual networks 473, including virtual private networks; virtual applications and operating systems 474; and virtual clients 475.

As an example, management layer 480 may provide the functions described below. Resource provisioning 481 provides dynamic procurement of computing resources and other resources that are utilized to perform tasks within the cloud-computing environment. Metering and Pricing 482 provide cost tracking as resources are utilized within the cloud-computing environment, and billing or invoicing for consumption of these resources. For example, these resources may include application software licenses. Security provides identity verification for cloud consumers and tasks, as well as protection for data and other resources. User portal 483 provides access to the cloud-computing environment for consumers and system administrators. Service level management 484 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 490 provides examples of functionality for which a cloud-computing environment (e.g., cloud computing environment 300) may be utilized. Examples of workloads and functions which may be provided from this layer include: navigation 491; software development and lifecycle management 492; virtual classroom education delivery 493; data analytics processing 494; transaction processing 495; and management 496. Management 496 may include functionality enabling the cloud-computing environment to be used to perform methodology according to any of the disclosed embodiments.

Group I Embodiments

Group I embodiments, pertain to systems, devices, and methods for market analytics and/or user recommendation of information (for example) to one or more users are provided. In such embodiments, the information corresponds to any one or more of media information (text/articles/publications, video, audio, combination thereof), products (any type of product, including financial products and stocks), and services, as well as other embodiments (e.g., see Summary and below). Specifically, Group I embodiments pertain generally to recommendations to one or more users of products/services/media/information/items base on an emotional impact factor.

With respect to embodiments for market analytics/user recommendation methods, such methodology includes identifying one or more correlations between at least one of one or more sentient agents and one or more non-sentient agents associated with corresponding systems, for example media platforms, and sales platforms, and the like. Additionally, such methodology includes determining at least one psychometric profile for each, the psychometric profile comprising an Emotional Impact Factor (EIF). Further, such methodology, in some embodiments, includes determining at least one market, and/or at least one recommendation using each EIF for at least one user. Thereafter, the at least one market and/or recommendation can be provided to at least one user.

Figure 5:
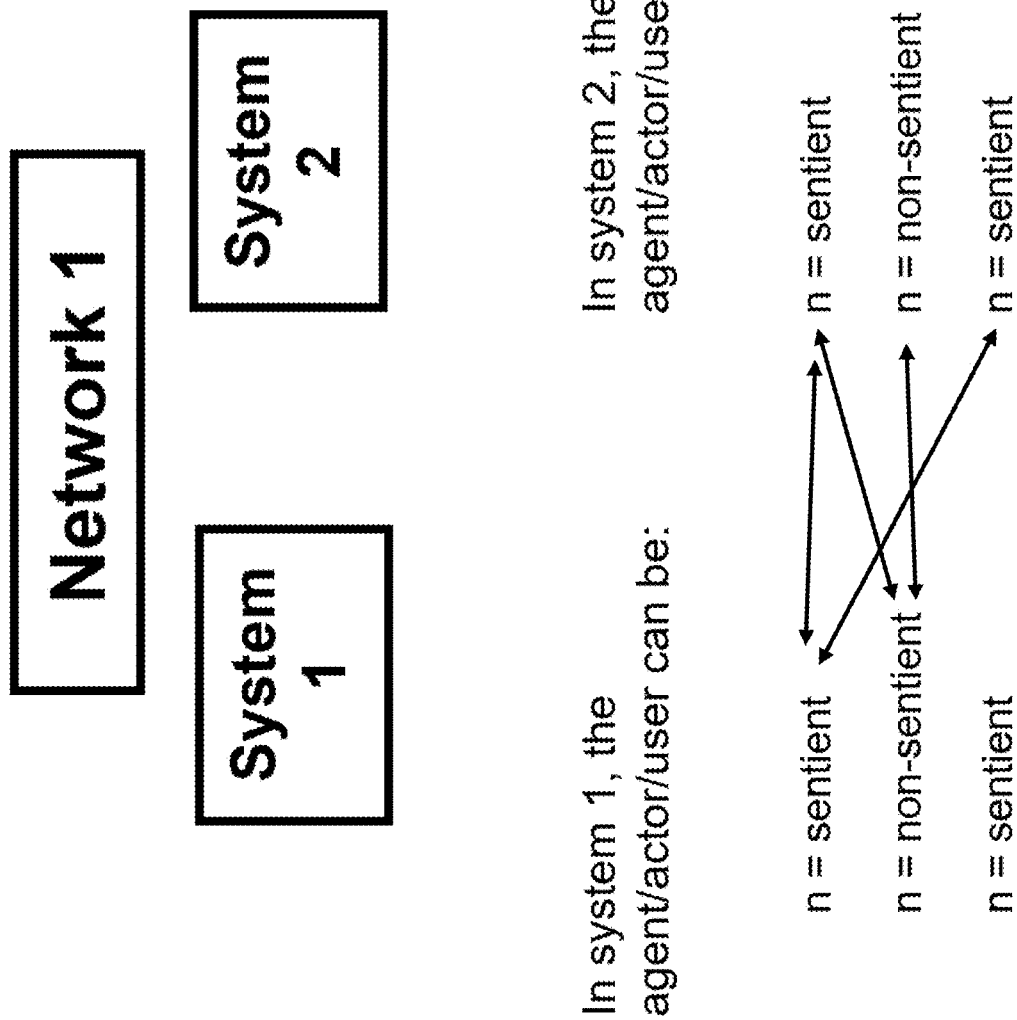
FIG. 5 is a block, schematic diagram of an overview of the methodology according to some embodiments of Group I.

To this end, FIG. 5, is a high-level overview of the methodology according to some embodiments. Accordingly, in the process of determining the EIF for actors/agents/entities (together "agents") in a plurality of networks (e.g., two) within a system. The agents can be either sentient or non-sentient. Matches are determined between structured and/or unstructured datasets, between hidden and visible layers (for example). Either network, as a whole (for example), can be sentient or non-sentient, as the process of determining EIF remains the same (according to some embodiments). An EIF can be understood, in the absence of a human actor, in terms of saturation or weighting. The factor that has the greatest weight within the network then replaces the equivalent of the strongest emotional factor.

For example, determining the EIF may comprise connecting a plurality of data points for identifying at least one parameter, such as, for example, data points associated with anthropological, ethnographic, and psychosocial factors. In some embodiments, determining the EIF includes integrating and/or weighting (according to methodology know to those skilled in the art) such one or more parameters, and/or integrating and/or weighting additional factors. Such additional factors include, for example, text-based analysis of annotations of information (e.g., of songs), indexing, media analysis, and principle component analysis. In some embodiments, determining the EIF may comprise or may further comprise examining structured or unstructured behavior data of a user or users. The structured and unstructured data may be from one or more defined networks and/or systems, where the defined networks and/or systems may comprise at least one of: streaming services, platforms (e.g., Netflix®, Hulu®, Amazon®), and peer-to-peer networks (together being referred to as "service(s)"). To this end, a respective EIF may be determined through an analysis of a limited number of parameter (e.g., in some embodiments $n>2$, $n>3$, $n>4$, $n>5$, $n>6$, $n>7$, $n>8$, $n>9$, $n>10$, $n>11$, or $n>12$ parameters).

The parameters include, for example, at least one of previous consumption within a given recommendation system and/or platform, and one or more peer-to-peer network transactions over a predetermined period of time. As noted above, such parameters/factors can be weighted, and in some embodiments, weighting is increased for transactions over the predetermined period of time.

The EIF, in some embodiments, may be configured for use for at least one of analyzing, visualizing, and recommending media content for at least one user, with the sentient agent configured to determine a relationship between at least one of a user's emotional quotient, psychometric profile, and the EIF of content available for consumption on a given media service.

In some embodiments, the EIF may be configured for use with a media recommendation system (e.g., publications, music, video), and may also be configured as a sales recommendation system configured to match at least one product to a user(s).

In some embodiments, a market analytics/user recommendation system is provided. Such a system, according to some embodiments, includes at least one processor having code operating thereon configured to cause the at least one processor to identify one or more correlations between at least one of one or more sentient agents and one or more non-sentient agents associated with corresponding systems, determine at least one psychometric profile for each, the psychometric profile comprising an Emotional Impact Factor (EIF), and determine at least one market, and/or at least one recommendation using each EIF for a user(s).

Such system embodiments (as well as others) may include one and/or another, and in some embodiments a plurality, and in some embodiments, structure and/or functionality for carrying out the foregoing methodology (for any such method embodiments) noted above. Moreover, some of the embodiments include devices, such as mobile devices (e.g., smartphones), running a mobile application which can work with system embodiments, such that, a user can receive recommendations on their mobile device (of course, mobile applications of service providers, media providers, streaming services can incorporate any of the above-noted functionality into their respective mobile applications). See General Embodiments above.

Some embodiments of the present disclosure are directed to systems, devices, and methods for a false-information/media (i.e., veracity) identification method. Such embodiments comprise reviewing one or more pieces of information/media, where each piece of media includes a source, determining at least one emotional impact factor (EIF) for each piece of media, and associating each EIF is a number or alphanumeric. The number or alphanumeric corresponds to a falseness scale, such that, in some embodiments, upon the associated EIF being greater than a predetermined threshold on the scale, the media may be flagged as false (or true, or presented to one or more users/viewers as a scale of veracity or falseness).

In some embodiments determination of the EIF may be configured for a specific audience, e.g., demographic. The audience or demographic may be one based on, for example, at least one of socio-economic status and educational level.

Such method embodiments may be embodied in a system comprising at least one processor having code operating thereon configured to cause the at least one processor to perform the methodology above. Such systems may be networked systems (e.g., via the internet) including one or more servers in communication with client/user computers accessing such systems to verify information/media.

Such system embodiments can further comprises a mobile application configured for operation on, used or in combination with a mobile application and/or device. Moreover, such a mobile application may be configured to at least one of send, receive, and/or process information from the at least one processor according to the disclosed system embodiments.

The veracity/falseness of reviewed information, in some embodiments, includes notifying a user(s)/consumer(s) of the one or more pieces of media of flagged false media, which can be done, via, for example, a user client computer, including, for example, a mobile device in wireless communication with the system. In addition to an in-application notification of the veracity of information, other forms of notification may be via text, phone, or email.

In some embodiments, the above-noted functionality can be incorporated into a media service's system, including, associated mobile applications.

Group II Embodiments

Embodiments of the present disclosure are directed to systems, devices, and methods for treating one or more brain functions, including neurological conditions and episodes associated therewith. Such embodiments determine OMM, which is hereinafter referred to as optimal medical media or OMM, which can be used to help treat a user suffering from a number of conditions associated with any number of brain functions, as well as being used for wellness. The OMM may be played through a user's audio/video device, including, for example, a smartphone operating a mobile application. Such embodiments can be configured to allay a fugue state, a panic attack, and achieve a dopaminergic state for a user.

Accordingly, in some embodiments, a brain function medical treatment method is provided, which can be performed by and/or in combination with a software system and/or application (and in some embodiments, a smartphone operating a mobile application) which determines one or more selections of the OMM. Such media comprises audio selections which are custom tailored to treat one or more brain functions, which may include neurological conditions and associated episodes thereof. Such OMM may be audio clips, segments (hereafter referred to as "pieces"), lasting from seconds, to minutes, to, in some embodiments, hours, and can be a single piece, or, a plurality of OMM pieces, which, in some embodiments, may be assembled together in one or more playlists. While some embodiments the OMM is audio content, in other embodiments, the OMM may be video content, or a combination of audio and video content.

In some embodiments, the OMM may comprise at least one song and includes a video component comprising lyrics corresponding to the at least one song configured such that the at least one user can sing the song. The OMM may also be selections derived or otherwise based on recorded compositions from Baroque, classical, and neoclassical periods, where the compositions may be augmented.

In some embodiments, the method includes (and associated system can be configured to) receiving first data corresponding to input from at least one patient (user) with respect to answers to a series questions (Q&A) regarding a brain function, or a condition or episode, corresponding to a brain function. In some embodiments, the questions are answered during a period when the user is not experiencing the condition or an associated episode. For example, such Q&A can include, for example, questions regarding anxiety, depression, etc. and variants within such as PTSD, and the like. Conditions can be, for example, weight issues (anorexia, obesity), concentration, anxiety disorders, distress, flow-state, general health, mood disorders, personality disorders, and stress; an episode can be, for example, a measurable or self-identified psychophysical disease or discomfort.

The method, in some embodiments, may also include selecting, by the user, one or more medical media parameters, or "MMP", which may comprise data associated with perspiration, heartrate, pulse, and/or other physiological response information, which can be used, in addition to the first data, to determine OMM for the user to help treat the condition or episode, and/or maintain wellness. In some embodiments, artificial intelligence (AI) may be used with at least one (and preferably both) of the first data and MMP, to determine the OMM. The AI may optionally comprise or include interaction with an AI bot (AIB), to aid in the identification of the OMM. The OMM is configured as a treatment or well-being plan for treating the episode or condition.

In some embodiments, the OMM is configured as at least one of one or more musical pieces, videos, and readings, which can then be configured into one or more playlists, each of which can be customized to treat (i.e., via playing and listening to the OMM via a media player such as a smartphone) a particular condition, disorder, and/or associated episode, as well as customized to maintain wellness (e.g., meditation).

For example, inspirational songs (e.g., songs about journeys, loving, and kindness) can be selected based on a user's particular tastes (which is determined based on at least one of the information garnered from the Q&A, and in some embodiments, the AI/AIB selections. Such AI/AIB selections may be trained based on at least one of the Q&A information, additional follow-up Q&A information (e.g., feedback information on previous playlist selections made by the system), secondary information (see below) or other information training sets (e.g., selected by medical/psychiatric professionals).

The OMM (including any configured playlists) can include a guiding component, which may be a medical professional voiceover (or AIB voiceover), guiding the user playing the OMM/playlist through the music, and/or managing the user through the treatment of the condition/disorder, or wellness (e.g., meditation).

A playlist may comprise a plurality of playlists each corresponding to a type including one or more of the following characteristics for the OMM of the playlist: variation of time signature, absence of minor keys, organic instrumentation, variation of instrumentation, absence of dissonance, balanced audio recording, limitation of decibel level, pre-set decibel level, familiarity, length of play, continuous play, intermission length, dopaminergic effect, and anxiolytic effect.

As noted above, the user (and/or medical/wellness professional) can provide feedback information into the system so as to not only train the AI/AIB for improved OMM selections for a particular user, but also to determine the efficacy of the OMM (e.g., efficacy can be determined for the OMM over a defined longitudinal application (e.g., measurable wellness, as a personalized medical tool). In some embodiments, the method/system can track secondary information, including, for example, health data, and personal data. The health data may comprise at least one of heartrate, blood pressure, and temperature, the personal data may comprise at least one of caloric intake, exercise/activity data, sleep data, medications, and fluid intake data. In some embodiments, reports can be produced which can list at least one of (and preferably several of or all of) data input, OMM selections, efficacy determination, feedback information, and the like.

In some embodiments, the system can be configured to identify an emergency or potential emergency, by determining aberrations in user-behavior, as well as to recognize patterns for a user so as to identify trends in the at least one user with respect to selection of specific words indicative of a condition for an associated brain function. In some embodiments, the system can be configured to determining using, for example, at least the secondary information, whether the user is within or outside of a state (e.g., a flow state, an emergency state).

The system may also be configured to notify at least one of the user and one or more individuals associated with the at least one user, e.g. regarding the at least one user having experienced or experiencing an episode, is suffering from a condition, and/or is within or outside of a state (which can utilize secondary information). Notification can be at least one of email, text, phone, and/or any method of secure direct in-application communication (e.g., notification, alert).

In some embodiments, the system may be configured to include an account for each user, accessible via a website, or via a mobile application. Such a system may be established such that use is paid for via, for example, advertisement, and/or, via traditional payments via user direct funding (e.g., credit card), or insurance. Funds may be collected/aggregating for each account from a third party (e.g., an insurance provider). In addition use (of funds) can be incentivized via the sale of data collected, analyzed, and/or otherwise produced (by system analyzation, AI, etc.).

In some embodiments, the system may be configured to select OMM so as to direct or otherwise train a user to develop new habits through behavior modification. Such training may include any (or at least one) of: centering, practicing neuro-feedback, and mindfulness, then returning to a state of productivity; delaying a length of time treatment of the at least one of the neurological episode and condition.

In some embodiments, the OMM may be manipulated by at least one of the at least one user, a medical professional, and via AI. For example, using AI, one or more STEMs associated with one or more pieces of the OMM can be produced (the OMM itself may comprise one or more STEMs). Such modifications may include, for example, manipulating the key of the OMM, and/or remixing a STEM(s) associated with the OMM.

Each STEM may correspond to a core element to an OMM piece/selection, and in some embodiments, comprise digital recordings of individual instruments, or a combination of instruments, or mixes thereof, for example, of a plurality of individual recorded tracks. For example, a percussion STEM can be a digital audio file of a bass drum, or a combination of different individual drums/components of a drum set (e.g., snare drum, cymbal, hi-hat, tom-tom, etc.), that when played, sounds like a complete drum set. A STEM may also be a particular song, or selection of music (e.g., Beethoven's Symphony No. 5 in C minor Op. 67).

In some embodiments, unique STEMs are created for particular OMM by training AI to manipulate, edit (e.g., content, length), and/or otherwise modified new or existing STEMs to customize them to treat or further a particular brain function (or condition, or episode associated therewith, or wellness). For example, each STEM can have an initial configuration with respect to tone, effects, compression, equalization, key and the like, perhaps for a particular brain function or condition. Individual STEMs can be so modified, and then mixed together to form yet further STEMs. The system, as noted above, may be configured to modify the STEMs and combine two or more, etc., to produce OMM for the particular brain function/condition/episode for treatment. STEMs may also be referred to as mixes (i.e., audio and/or video tracks, processed separately prior to combining them into a master mix or master STEM. A STEM may also be referred to as sub-mix, a sub-group, or a bus.

For the AI to modify a STEM(s), a user can select at least one parameter, and then the AI can compose one or more pieces of the OMM by mixing/re-mixing one or more STEMs associated with the OMM (for example). The AI can be trained to manipulate previously produced (and stored) and new STEMs so as to determine OMM for a particular user for a particular brain function (condition and/or episode associated therewith). Thus, in some embodiments, the determined OMM (and corresponding playlist(s)) can be configured by the system to interact with one another to produce a desired affect.

In some embodiments, a brain function medical treatment system is provided and comprises or otherwise includes at least one processor having code operating thereon configured to cause the at least processor to conduct the above noted steps for methods to treat one or more brain functions, conditions corresponding thereto, and episodes associated therewith, with OMM. The at least one processor may comprise one or more servers, and/or computers, as well as a mobile application for users (and in some embodiments, administrators of the system) to make use of the OMM. Such a mobile application may be configured to at least one of send, receive, and/or process information from the at least one processor.

In some embodiments, the system is established a set of stored STEMs for producing the OMM for users; such stored STEMs may also be referred to as core STEMs. From this, using information provided by the user, a medical professional, and/or AI, OMM is determined for a user for a brain function/condition, and then preferably assembled into a playlist. Particularly, in some embodiments, AI is used to modify one or more of the stored STEMS so as to customize it for a particular user and for a particular brain function/condition.

Figure 6:
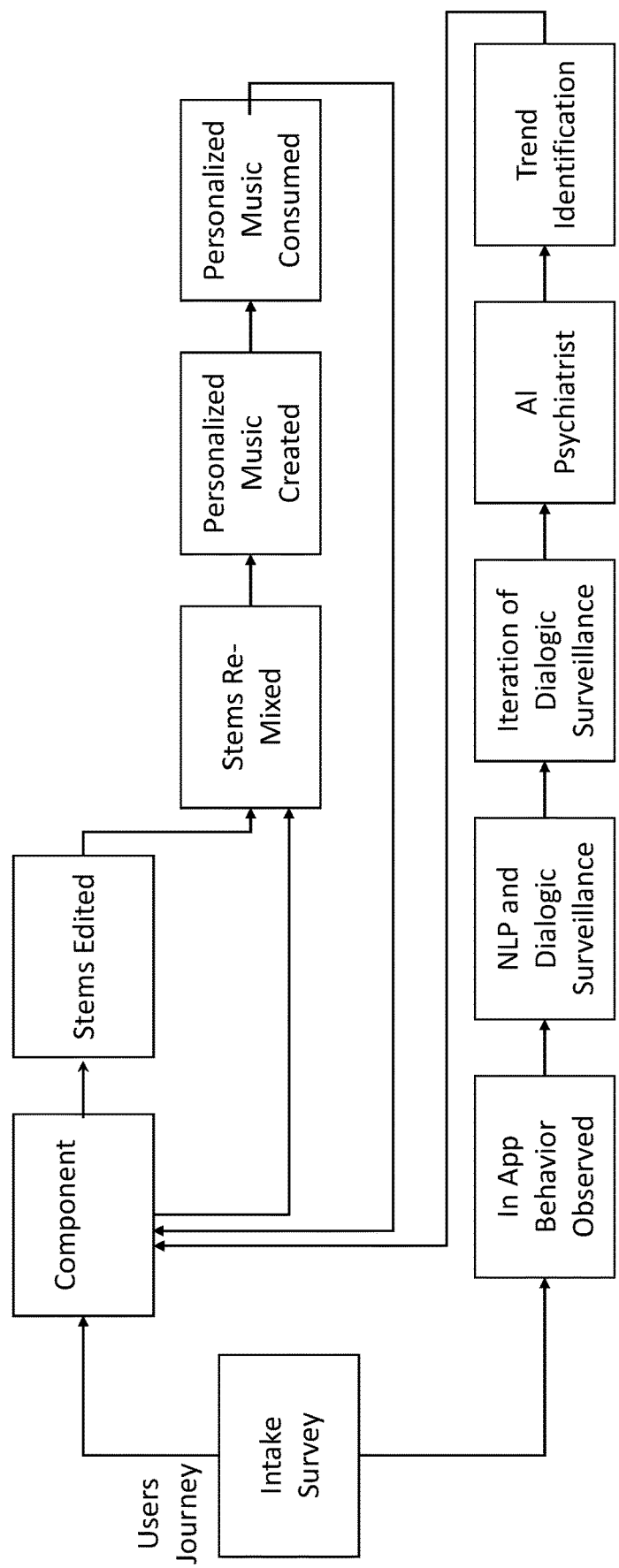
FIG. 6 is a block, schematic diagram of an overview of the methodology according to some embodiments of Group II.

FIG. 6 illustrates a flow diagram depicting an exemplary process according to some embodiments. As shown, a user seeking treatment may first answer questions for a survey or questionnaire via a mobile application regarding a brain function or condition that the user wishes to seek treatment. From the answers which are uploaded into the system (e.g., a server), and component core STEMs are selected. In view of the answers provided, the selected STEMs are then modified and or edited and/or modified so as to be customized for the particular user and condition. Thereafter, the STEMs are then remixed which results in OMM ("Personalized Music Created"), and then used by the user (e.g., via a smartphone application). The OMM and associated STEMs can be stored and become core STEMs.

The mobile application which plays the OMM for the user may also be configured to monitor user behavior and store and/or upload data associated with such behavior to the server. The mobile application may also interact in real-time (or near real-time, "real-time" is hereinafter any communication or event that happens in current time or near current time) with AI, or the AIB, via spoken or typed responses; in some embodiments, such user behavior may be monitored in real-time via the sensors provided in the smartphone/mobile device that the mobile application is operating. Through natural language processing (NLP/dialogic), the spoken and monitored behavior is interpreted by the AIB, and the AIB can respond via typed or spoken word (e.g., using Siri, for example, in IOS® devices).

By use and repetitive use of the OMM and refined OMM determined by the system and used by the user, the AI/AIB identify trends. Such trends can then be used in future iterations of OMM selections for the particular user, or other users having similar personality trains/survey answers who are seeking like treatment.

While various inventive embodiments have been described and illustrated herein, those having ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all structure, parameters, dimensions, materials, functionality, and configurations described herein are meant to be an example and that the actual structure, parameters, dimensions, materials, functionality, and configurations will depend upon the specific application or applications for which the inventive teachings is/are used.

Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the claims supported by the present disclosure, and equivalents thereto, inventive embodiments may be practiced otherwise than as specifically described and claimed. Inventive embodiments of the present disclosure are also directed to each individual feature, system, article, structure, material, kit, functionality, step, and method described herein. In addition, any combination of two or more such features, systems, articles, structure, materials, kits, functionalities, steps, and methods, if such are not mutually inconsistent, is included within the inventive scope of the present disclosure. Some embodiments may be distinguishable from the prior art for specifically lacking one or more features/elements/functionality (i.e., claims directed to such embodiments may include negative limitations).

Also, as noted, various inventive concepts are embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terminology used herein was chosen to best explain the principles of the one or more embodiments, practical applications, or technical improvements over current technologies, or to enable understanding of the embodiments disclosed herein. As described, details of well-known features and techniques may be omitted to avoid unnecessarily obscuring the embodiments of the present disclosure.

References in the specification to "one embodiment," "an embodiment," "an example embodiment," or the like, indicate that the embodiment described may include one or more particular features, structures, or characteristics, but it shall be understood that such particular features, structures, or characteristics may or may not be common to each and every disclosed embodiment of the present disclosure herein. Moreover, such phrases do not necessarily refer to any one particular embodiment per se. As such, when one or more particular features, structures, or characteristics is described in connection with an embodiment, it is submitted that it is within the knowledge of those skilled in the art to affect such one or more features, structures, or characteristics in connection with other embodiments, where applicable, whether or not explicitly described.

What is currently claimed:

1. A brain function medical treatment method comprising:
providing at least one server;
providing a series of questions for a user to provide answers thereto, the answers comprising first data;
gathering first data by the server from a user via a user interface of an application program operational on or accessible via a smart device of the user;
selection, by the user via the user interface, at least one medical media parameter, the at least one medical media parameter comprising or corresponding to a neurological disorder;
automatically identifying, via the server, a treatment for the user, the identified treatment comprising an optimal medical media (OMM) based on at least the first data and the selected at least one medical media parameter, and
administering the treatment by playing or otherwise presenting the OMM via the user's smart device,
wherein:
the OMM:
is configured to counteract the neurological disorder so as to keep the user from entering at least one of a fugue state and a dissociative state,
comprises at least one audio clip, or one or more segments thereof, such audio clip or segment thereof includes an associated STEM corresponding to a core element, and
the core element comprising any and all of an individual instrument and a mix of a combination of instruments;
and
modifying, via the user interface, at least one STEM of an associated audio clip or segment thereof, by manipulating any and all of: the key, the STEM mix, the tone, one or more effects, the compression, and/or equalization.

2. The method of claim 1, wherein:
the OMM comprises any and all of
a guiding component, one or more videos, and one or more readings,
and
the method further comprises determining an efficacy of the OMM for the user with respect to the neurological disorder.

3. The method of claim 2, wherein:
the neurological disorder is selected from the group consisting of: distress, flow-state, weight issues, concentration, anxiety disorders, general health, mood disorders, personality disorders, and stress;
and
determining the efficacy comprises:
collecting feedback information from the user's smart device on use of the OMM for treatment of the neurological disorder,
and
the feedback information includes secondary information comprising at least one of health data, and personal data.

4. The method of claim 1, wherein the server is further configured to:
collect, via the user interface, medication data of the user,
using at least one of user selection of the at least one medical media parameter, feedback information, secondary information, and medication information, the at least one server is additionally configured for:
identifying an emergency or potential emergency by aberrations in user behavior,
recognizing one or more patterns for the user so as to identify trends in the user with respect to selection of specific words indicative of a neurological disorder, and
determining, based on at least secondary information, whether the user is within or outside of a flow state or an emergency state.

5. The method of claim 1, wherein the treatment further comprises:
training the user, using the OMM, to develop habits through behavior modification, and
training comprises any and all of centering, practicing neuro-feedback, and mindfulness, then returning to a state of productivity.

6. The method of claim 1, wherein the treatment is configured to allay any and all of a fugue state, a panic attack, and achieve a dopaminergic state in the user.

7. The method of claim 1, wherein the OMM further comprises a plurality of playlists each corresponding to a playlist type including any and all of the following characteristics: variation of time signature, absence of minor keys, instrumentation, variation of instrumentation, absence of dissonance, balanced audio recording, limitation of decibel level, pre-set decibel level, familiarity, length of play, continuous play, intermission length, dopaminergic effect, and anxiolytic effect.

8. The method of claim 1, wherein the OMM comprises at least one song including a video component comprising lyrics corresponding to the at least one song configured such that the user can sing the song.

9. The method of claim 1, wherein the at least one audio clip comprises a plurality of audio clips each including an associated STEM.

10. The method of claim 9, further comprising revising treatment by remixing the plurality of STEMs of the OMM.

11. The method of claim 1, wherein the at least one STEM corresponds to a core element of the OMM.

12. The method of claim 9, wherein:
   each STEM of the plurality of STEMs corresponds to a respective core element, and
   the core elements for the plurality of STEMs are configured to interact with one another to produce a desired effect.

13. The method of claim 1, repeating the gathering first data step and/or selecting step, and the treatment step.

14. The method of claim 1, where the at least one audio clip comprises a composition.

15. The method of claim 14, wherein the composition is augmented.

* * * * *